(12) United States Patent
Goldstein et al.

(10) Patent No.: US 10,750,987 B2
(45) Date of Patent: *Aug. 25, 2020

(54) DRUG DELIVERY DEVICE WITH ELECTRICALLY CONTROLLED VOLUME CHANGING MEANS

(71) Applicant: SteadyMed Ltd., Rehovot (IL)

(72) Inventors: Jonathan Goldstein, Jerusalem (IL); Niles Fleischer, Rehovot (IL); Nir Rotem, Katzir (IL); Lior Bar-Gat, Holon (IL); Vladimir Piskosh, Petah Tikva (IL)

(73) Assignee: SteadyMed Ltd., Rehovot (IL)

( * ) Notice: Subject to any disclaimer, the term of this patent is extended or adjusted under 35 U.S.C. 154(b) by 125 days.

This patent is subject to a terminal disclaimer.

(21) Appl. No.: 15/634,880

(22) Filed: Jun. 27, 2017

(65) Prior Publication Data

US 2018/0035935 A1     Feb. 8, 2018

Related U.S. Application Data

(63) Continuation of application No. 13/956,965, filed on Aug. 1, 2013, now Pat. No. 9,687,186, which is a
(Continued)

(30) Foreign Application Priority Data

Jul. 21, 2005   (IL) ........................................ 169807
May 7, 2006   (IL) ........................................ 175460

(51) Int. Cl.
   *H01M 2/02*       (2006.01)
   *A61B 5/157*      (2006.01)
   (Continued)

(52) U.S. Cl.
   CPC .......... *A61B 5/157* (2013.01); *A61B 5/15003* (2013.01); *A61B 5/150992* (2013.01);
   (Continued)

(58) Field of Classification Search
   CPC .................... A61M 5/155; A61M 2005/14204
   See application file for complete search history.

(56) References Cited

U.S. PATENT DOCUMENTS 3,642,540 A *   2/1972   Argent ................. H01M 12/06
                                                         29/623.3
4,842,598 A      6/1989   Tran
                  (Continued)

FOREIGN PATENT DOCUMENTS

AT            497105 T      2/2011
AU      2007345767 B2    7/2013
          (Continued)

OTHER PUBLICATIONS

Lee et al., "Battery Dimensional Changes Occuring During Charge/Discharge Cycles—Thin Rectangular Lithium Ion and Polymer Cells," Journal of Power Sources, 119-121: 833-837 (2003).

*Primary Examiner* — Maria Laios
(74) *Attorney, Agent, or Firm* — Kilpatrick Townsend & Stockton LLP

(57) ABSTRACT

Embodiments of the present invention provide drug-delivery devices comprising a drug reservoir chamber containing a substance to be delivered, in fluid connection with a drug administration means, and at least one displacement-generating battery cell coupled to said drug reservoir chamber by a coupling means, the at least one displacement-generating battery cell comprising an element that changes shape as a result of discharge of the battery cell so as to cause a displacement within the battery unit, the arrangement being such that the displacement derived from said battery unit is conveyed by said coupling means to cause displacement of
(Continued)

at least a portion of a wall of said drug reservoir chamber reducing the volume of said drug reservoir chamber such that said substance is expelled from said drug reservoir chamber towards said drug administration means upon discharge, thereby being a self-powered drug delivery device.

17 Claims, 27 Drawing Sheets

Related U.S. Application Data continuation-in-part of application No. 11/996,468, filed as application No. PCT/IL2006/000769 on Jul. 3, 2006, now Pat. No. 9,011,376, said application No. 13/956,965 is a continuation-in-part of application No. 12/299,602, filed as application No. PCT/IL2007/000548 on May 6, 2007, now Pat. No. 8,834,454.

(51) Int. Cl.
  *A61M 5/145* (2006.01)
  *A61B 5/15* (2006.01)
  *A61M 5/142* (2006.01)

(52) U.S. Cl.
  CPC ...... *A61M 5/1452* (2013.01); *A61M 5/14526* (2013.01); *A61M 2005/14204* (2013.01); *H01M 2002/0205* (2013.01)

(56) References Cited

U.S. PATENT DOCUMENTS

| | | | |
|---|---|---|---|
| 4,842,963 A * | 6/1989 | Ross, Jr. | ............... H01M 4/244 29/623.1 |
| 4,843,598 A | 6/1989 | Medlin | |
| 4,886,514 A | 12/1989 | Maget | |
| 5,062,834 A | 11/1991 | Gross et al. | |
| 5,102,389 A | 4/1992 | Hauser | |
| 5,108,852 A | 4/1992 | Tomantschger et al. | |
| 5,109,850 A | 5/1992 | Blanco et al. | |
| 5,134,046 A | 7/1992 | Chow et al. | |
| 5,318,557 A | 6/1994 | Gross | |
| 5,354,264 A | 10/1994 | Bae et al. | |
| 5,436,372 A | 7/1995 | Yoshida et al. | |
| 5,438,249 A | 8/1995 | Chang et al. | |
| 5,505,706 A | 4/1996 | Maus et al. | |
| 5,527,288 A | 6/1996 | Gross et al. | |
| 5,563,004 A | 10/1996 | Buzzelli et al. | |
| 5,643,207 A | 7/1997 | Rise | |
| 5,677,083 A | 10/1997 | Tomiyama | |
| 5,814,020 A * | 9/1998 | Gross | ............... A61M 5/14248 604/141 |
| 5,827,233 A | 10/1998 | Futagawa et al. | |
| 5,848,991 A | 12/1998 | Gross et al. | |
| 5,938,640 A | 8/1999 | Maget et al. | |
| 5,980,741 A | 11/1999 | Schnell et al. | |
| 6,150,053 A | 11/2000 | Murata et al. | |
| 6,186,982 B1 | 2/2001 | Gross et al. | |
| 6,296,967 B1 | 10/2001 | Jacobs et al. | |
| 6,312,409 B1 | 11/2001 | Gross | |
| 6,322,532 B1 | 11/2001 | D'Sa et al. | |
| 6,358,239 B1 | 3/2002 | Rake et al. | |
| 6,377,848 B1 | 4/2002 | Garde et al. | |
| 6,400,489 B1 | 6/2002 | Suzuki et al. | |
| 6,465,125 B1 | 10/2002 | Takami et al. | |
| 6,506,520 B1 | 1/2003 | Inoue et al. | |
| 6,534,218 B1 | 3/2003 | Okada et al. | |
| 6,537,249 B2 | 3/2003 | Kriesell et al. | |
| 6,537,250 B1 * | 3/2003 | Kriesel | ............ A61M 5/14248 604/132 |
| 6,577,039 B2 | 6/2003 | Ishida et al. | |
| 6,589,229 B1 | 7/2003 | Connelly et al. | |
| 6,733,485 B1 | 5/2004 | Whitehurst et al. | |
| 6,982,514 B1 | 1/2006 | Lu et al. | |
| 7,242,134 B2 | 7/2007 | Wallace et al. | |
| 7,364,568 B2 | 4/2008 | Angel et al. | |
| 7,541,715 B2 | 6/2009 | Chiang et al. | |
| 7,828,771 B2 | 11/2010 | Chiang et al. | |
| 7,872,396 B2 | 1/2011 | Chiang et al. | |
| 7,923,895 B2 | 4/2011 | Chiang et al. | |
| 7,994,686 B2 | 8/2011 | Chiang et al. | |
| 7,999,435 B2 | 8/2011 | Chiang et al. | |
| 8,093,781 B2 | 1/2012 | Chiang et al. | |
| 8,247,946 B2 | 8/2012 | Chiang et al. | |
| 8,310,130 B2 | 11/2012 | Chiang et al. | |
| 8,378,552 B2 | 2/2013 | Chiang et al. | |
| 8,604,664 B2 | 12/2013 | Chiang et al. | |
| 8,834,454 B2 | 9/2014 | Genosar et al. | |
| 8,952,595 B2 | 2/2015 | Huang | |
| 9,011,376 B2 | 4/2015 | Genosar et al. | |
| 9,724,462 B2 | 8/2017 | Rotem | |
| 2002/0039620 A1 | 4/2002 | Mohsen Shahinpoor et al. | |
| 2002/0107480 A1 | 8/2002 | Kriesel et al. | |
| 2002/0156461 A1 * | 10/2002 | Joshi | ................ A61M 5/14244 604/891.1 |
| 2002/0169439 A1 | 11/2002 | Flaherty | |
| 2003/0014014 A1 | 1/2003 | Nitzan | |
| 2003/0205582 A1 | 11/2003 | Joshi et al. | |
| 2004/0059282 A1 | 3/2004 | Flock et al. | |
| 2004/0068224 A1 | 4/2004 | Couvillon et al. | |
| 2004/0115068 A1 | 6/2004 | Hansen et al. | |
| 2004/0115523 A1 | 6/2004 | Hommura et al. | |
| 2004/0115530 A1 | 6/2004 | Maeda et al. | |
| 2004/0138612 A1 | 7/2004 | Shermer et al. | |
| 2005/0096587 A1 | 5/2005 | Santini et al. | |
| 2006/0052768 A1 * | 3/2006 | Joshi | ................... A61K 9/0004 604/892.1 |
| 2006/0069344 A1 | 3/2006 | Southam et al. | |
| 2006/0102455 A1 | 5/2006 | Chiang et al. | |
| 2006/0106346 A1 | 5/2006 | Sullivan et al. | |
| 2006/0200073 A1 | 9/2006 | Radmer et al. | |
| 2008/0188779 A1 | 8/2008 | Vellero | |
| 2008/0281270 A1 | 11/2008 | Cross et al. | |
| 2009/0069746 A1 | 3/2009 | Miller et al. | |
| 2009/0093772 A1 | 4/2009 | Genosar et al. | |
| 2010/0022992 A1 | 1/2010 | Genosar et al. | |
| 2010/0056874 A1 | 3/2010 | Dijksman et al. | |
| 2010/0130931 A1 | 5/2010 | Yodfat et al. | |
| 2010/0152658 A1 | 6/2010 | Hanson et al. | |
| 2010/0266638 A1 | 10/2010 | Turkel et al. | |
| 2010/0274221 A1 | 10/2010 | Sigg et al. | |
| 2011/0098652 A1 | 4/2011 | Haster et al. | |
| 2011/0098676 A1 | 4/2011 | Chiang et al. | |
| 2011/0160655 A1 | 6/2011 | Hanson et al. | |
| 2011/0306929 A1 | 12/2011 | Levesque et al. | |
| 2012/0041338 A1 | 2/2012 | Chickering, III | |
| 2012/0042517 A1 | 2/2012 | Tronnes et al. | |
| 2012/0238849 A1 | 9/2012 | Holtzclaw et al. | |
| 2013/0020903 A1 | 1/2013 | Chiang et al. | |
| 2013/0249348 A1 | 9/2013 | Chiang et al. | |
| 2014/0148761 A1 | 5/2014 | Rotem et al. | |
| 2014/0163339 A1 | 6/2014 | Goldstein et al. | |
| 2014/0171867 A1 | 6/2014 | Walsh et al. | |
| 2015/0017493 A1 | 1/2015 | Genosar et al. | |
| 2015/0038907 A1 | 2/2015 | Rotem | |
| 2015/0045718 A1 | 2/2015 | Shlomo | |
| 2016/0361491 A1 | 12/2016 | Shaked et al. | |
| 2017/0304532 A1 | 10/2017 | Rotem | |

FOREIGN PATENT DOCUMENTS

| | | |
|---|---|---|
| BR | PI0715482 A2 | 5/2014 |
| CA | 2570092 A1 | 12/2005 |
| CA | 2812877 A1 | 4/2012 |
| CA | 2665996 C | 7/2015 |
| CN | 101589230 B | 2/2012 |
| DE | 3621846 A1 | 1/1988 |
| DE | 19809483 A1 | 9/1999 |
| EP | 0676214 A1 | 10/1995 |
| EP | 1621875 B1 | 10/2007 |
| EP | 1912690 A1 | 4/2008 |
| EP | 1784890 A4 | 4/2010 |

(56) References Cited

FOREIGN PATENT DOCUMENTS

| | | |
|---|---|---|
| EP | 2049791 B1 | 1/2011 |
| EP | 2366896 A2 | 9/2011 |
| EP | 2621558 A1 | 8/2013 |
| EP | 2538080 A3 | 10/2014 |
| EP | 2825225 A1 | 1/2015 |
| EP | 2827923 A1 | 1/2015 |
| ES | 2358951 T3 | 5/2011 |
| GB | 2221394 A | 2/1990 |
| HK | 1131814 A1 | 9/2011 |
| IL | 169807 | 2/2006 |
| IL | 179942 A | 1/2012 |
| IL | 196708 A | 2/2015 |
| JP | 02-131376 A | 5/1990 |
| JP | 04-127885 A | 4/1992 |
| JP | 2001144342 A | 5/2001 |
| JP | 2008503059 A | 1/2008 |
| JP | 2009545290 A | 12/2009 |
| JP | 2013030481 A | 12/2009 |
| KR | 20090046863 A | 5/2009 |
| MX | 2009000997 A | 5/2009 |
| RU | 2453730 C2 | 6/2012 |
| WO | 95/15589 A1 | 6/1995 |
| WO | 1997/010012 A1 | 3/1997 |
| WO | 2001/021234 A1 | 3/2001 |
| WO | 01/51108 A1 | 7/2001 |
| WO | 2002/069935 A1 | 9/2002 |
| WO | 2004/006982 A2 | 1/2004 |
| WO | 2004/067066 A1 | 8/2004 |
| WO | 2005/124918 A2 | 12/2005 |
| WO | 2007/010522 A1 | 1/2007 |
| WO | 2007/129317 A1 | 11/2007 |
| WO | 2008/062335 A1 | 5/2008 |
| WO | 2005124918 A3 | 5/2008 |
| WO | 2008036122 A3 | 7/2008 |
| WO | 2008/122983 A1 | 10/2008 |
| WO | 2008094196 A3 | 11/2008 |
| WO | 2009123672 A3 | 7/2010 |
| WO | 2011/075100 A1 | 6/2011 |
| WO | 2012/042517 A1 | 4/2012 |
| WO | 2013/136327 A1 | 9/2013 |
| WO | 2013/140395 A1 | 9/2013 |
| ZA | 200900834 B | 5/2010 |

\* cited by examiner

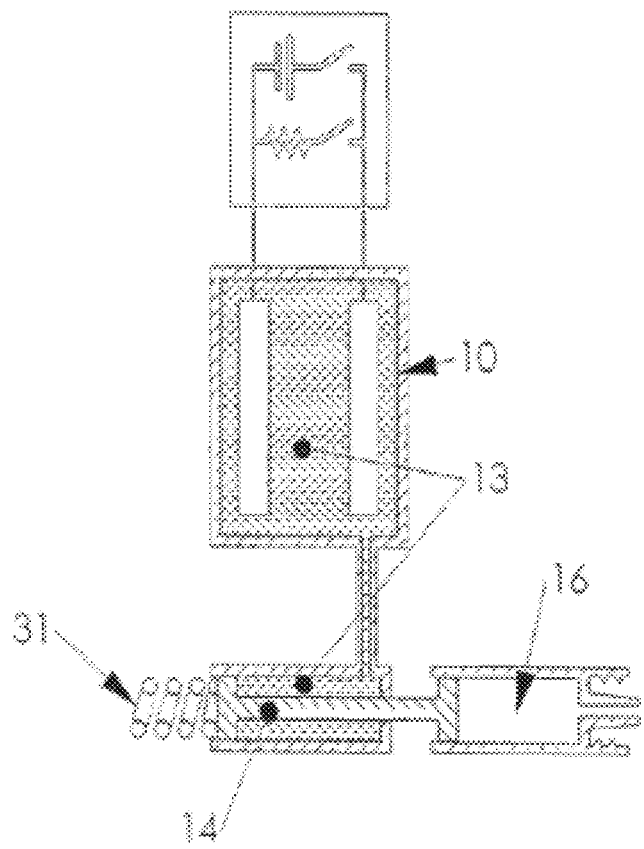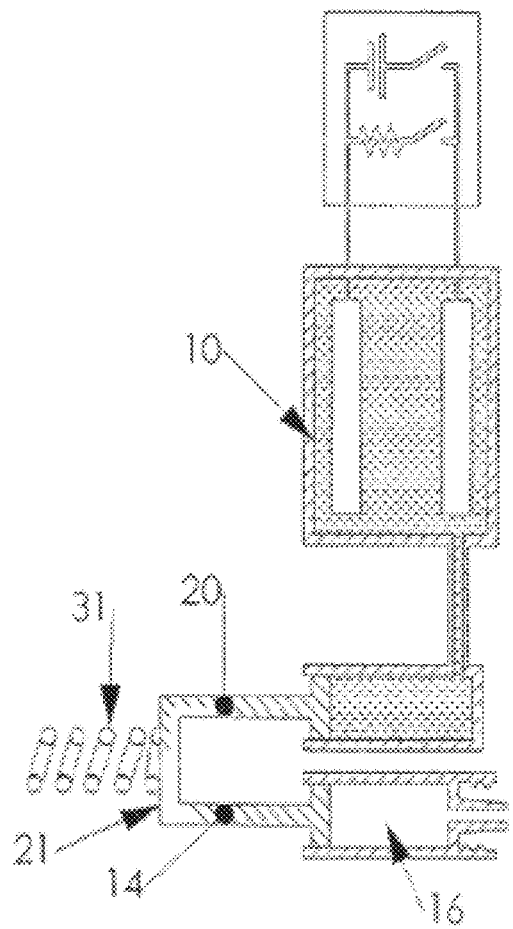
FIG. 3A
FIG. 3B

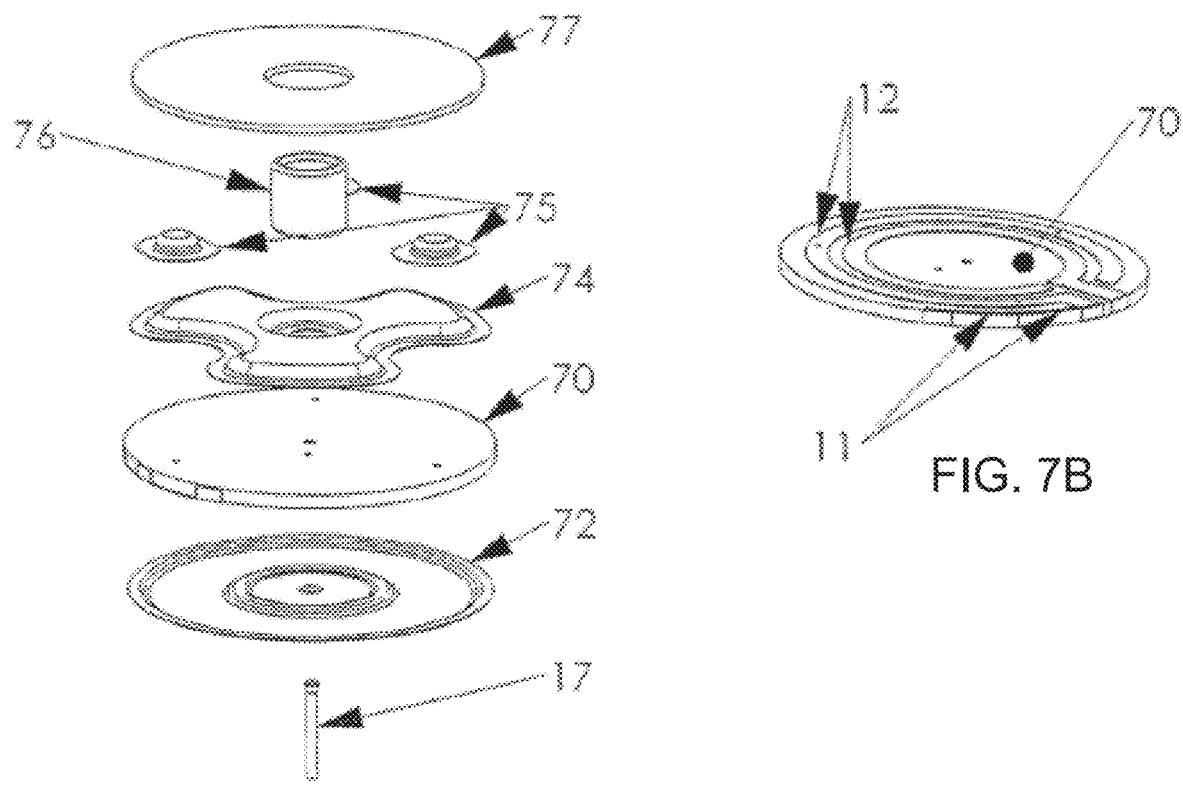
FIG. 7A
FIG. 7B
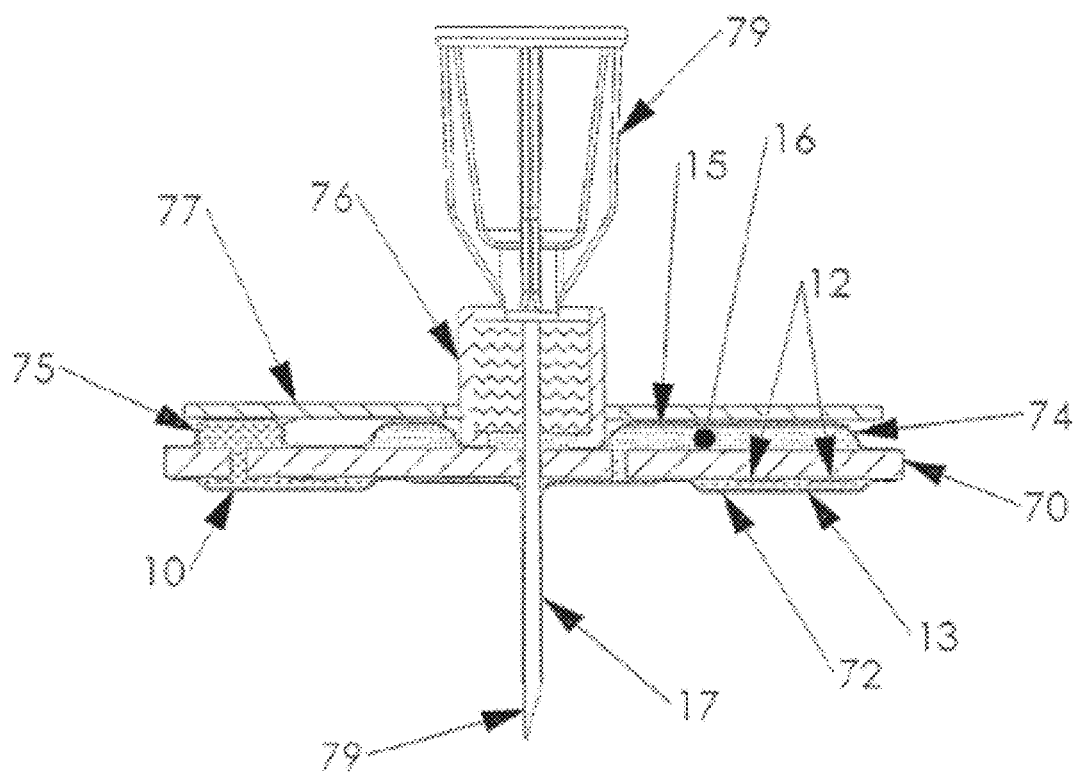
FIG. 7C

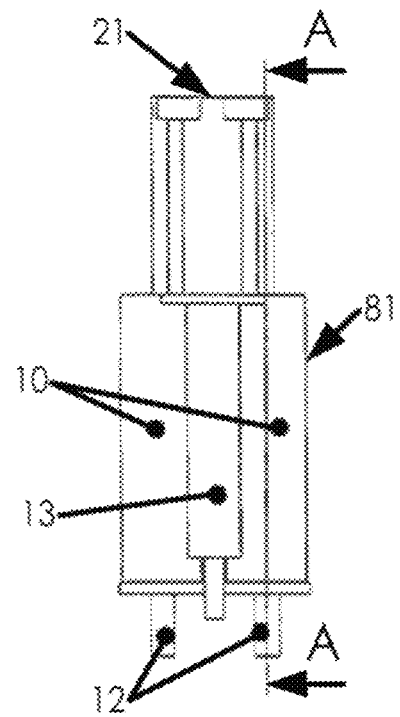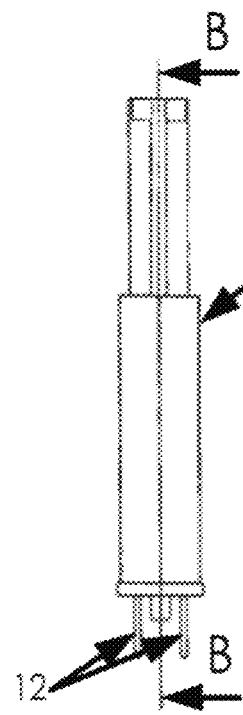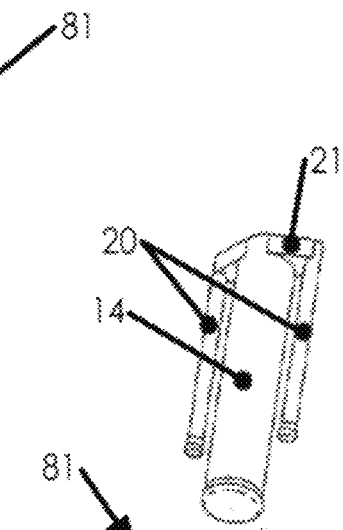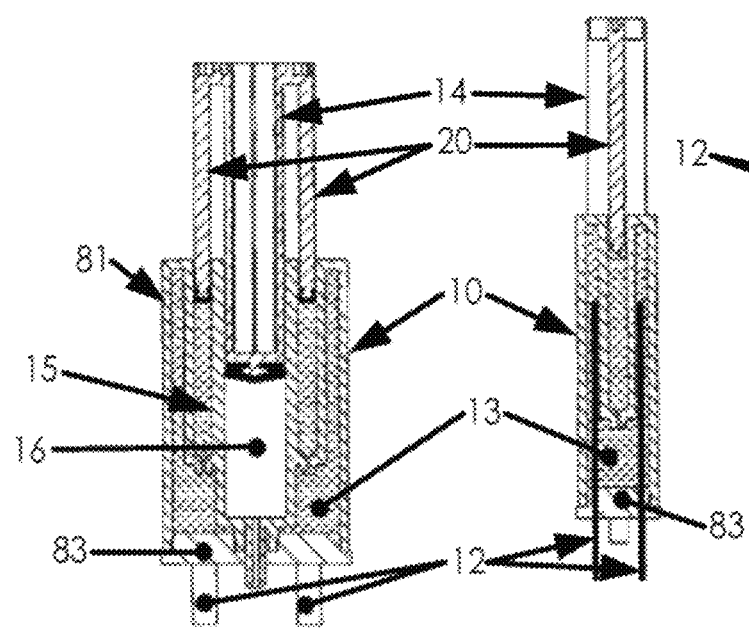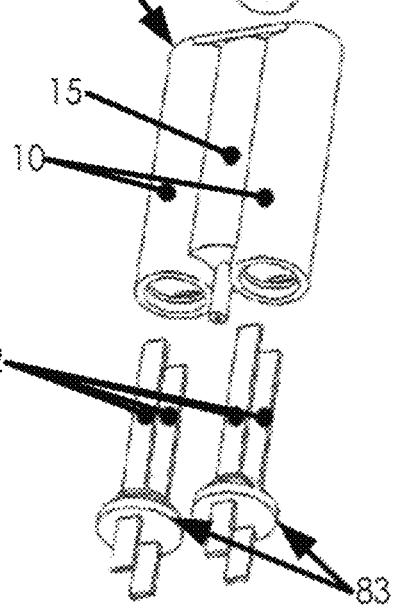
FIG.8B
FIG.8C
FIG.8A
FIG.8D
FIG.8E

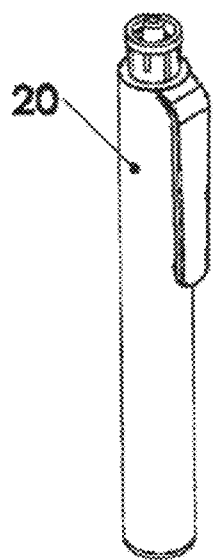
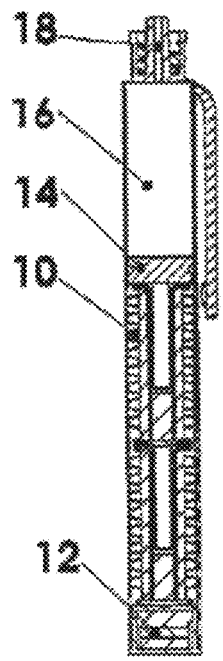
FIG. 13A   FIG. 13B
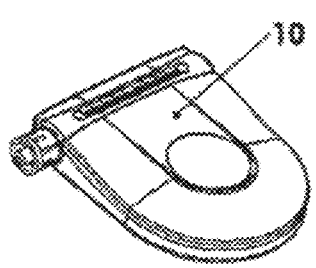
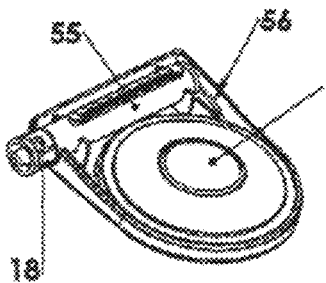
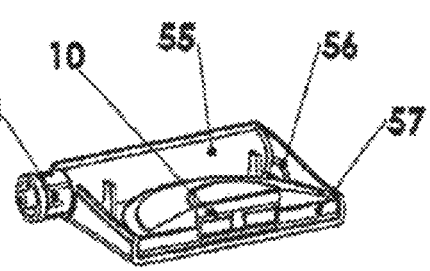
FIG. 13C   FIG. 13D   FIG. 13E

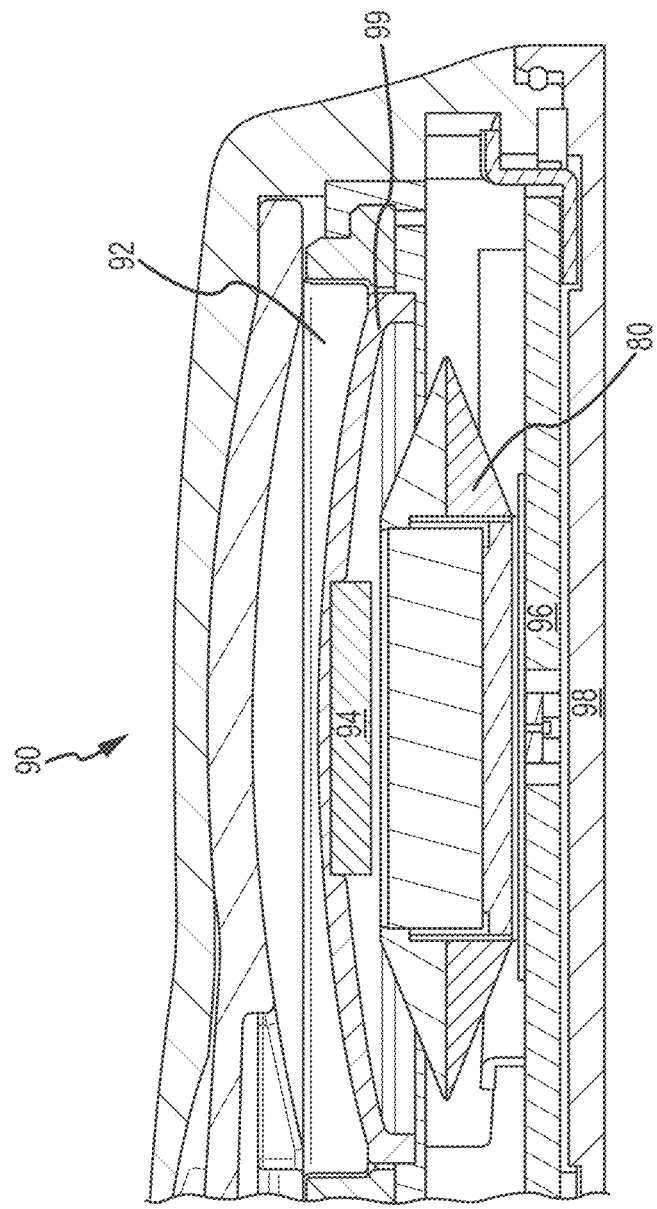

PATCH-TYPE PUMP 1600

ATTACHMENT MEANS 1610

BODY OF USER 1620

FIG. 16

MEANS FOR MIXING 1810

DRUG-DELIVERY DEVICE 1800

FIG. 18

MEANS FOR SAMPLING BODY FLUIDS 2010

DRUG-DELIVERY DEVICE 2000

FIG. 20

COMMUNICATION MEANS 2110

DRUG-DELIVERY DEVICE 2100

FIG. 21

SAFETY FEATURE 2210

DRUG-DELIVERY DEVICE 2200

FIG. 22

DRUG DELIVERY DEVICE WITH ELECTRICALLY CONTROLLED VOLUME CHANGING MEANS

CROSS-REFERENCES TO RELATED APPLICATIONS

This application is a continuation of U.S. patent application Ser. No. 13/956,965 filed Aug. 1, 2013, which is a continuation-in-part of U.S. patent application Ser. No. 11/996,468 filed Nov. 19, 2008, now U.S. Pat. No. 9,011,376 issued Apr. 21, 2015, which is a § 371 National Stage of International Application No. PCT/IL2006/000769 filed Jul. 3, 2006, which claims the benefit of priority to Israeli Patent Application No. 169,807 filed Jul. 21, 2005. U.S. patent application Ser. No. 13/956,965 filed Aug. 1, 2013 is also a continuation-in-part of U.S. patent application Ser. No. 12/299,602 filed Feb. 2, 2004, now U.S. Pat. No. 8,834,454 issued Sep. 16, 2014, which is a § 371 National Stage of International Application No. PCT/IL2007/000548 filed May 6, 2007, which claims the benefit of priority to Israeli Patent Application No. 175,460 filed May 7, 2006. This application is related to International Application Nos. PCT/IL2008/000549 filed Apr. 27, 2008 and PCT/IL2011/000757 filed Sep. 26, 2011. The entire content of each of the above filings is incorporated herein by reference for all purposes.

BACKGROUND OF THE INVENTION

Embodiments of the present invention relate to the field of drug delivery and encompass drug-delivery devices driven by an electrically-controlled displacement-generating battery cell. More particularly, embodiments of the present invention relate to an electrically-controlled non-gas evolution dependent volume-changing or shape-changing electrochemical cell, which drives a drug-delivery mechanism, wherein the delivery rate can be very precisely controlled.

There are numerous kinds of electrochemical cells, the common element being that applying an electrical charge to or removing an electrical charge from such a cell causes an electrochemical change, and in some cases a derived chemical change in the electrodes, and in some cases also the electrolyte of such cell. Many types of electrochemical cells comprise electrodes and electrolyte, in which the chemical reaction between said chemicals in the cell is driven by discharging or charging said electrodes. Such a cell can be either a passive cell or a battery cell. In a passive cell, electricity needs to be introduced into the cell in order to "drive" the chemical reaction. In a battery cell or fuel cell, the cell itself generates electricity as the reaction runs, providing that a discharge circuit is connected to the cell positive and negative poles. In the case of a passive cell (or a battery on charge), the rate of reaction is determined by the electrical power applied; whereas in a battery cell which is discharging, the control over the energy consumption determines the rate of discharge of the battery. The definition of battery cells herein includes not only conventional types of batteries (using either "wet" or "dry" chemistry) but also (a) lithium "shuttle" type batteries in which the process is that ions in the electrolyte shuttle back and forth between the electrodes as opposed to participating in a conventional chemical reaction; and (b) sealed fuel cells in which a fixed starting amount of fuel is used up as the cell discharges. Embodiments of the present invention apply to all the above types of cells, providing only that the electrochemical and/or derived chemical process involved is such that it causes a volume change or shape change within the cell as the process proceeds.

In the field of battery cells, the volume change generated as the battery charges or discharges is a known yet undesirable side effect, said effect being mentioned in the various references. For example, US Patent Publication No. 2004/0115530 describes a method of preventing the detrimental effects of the volume change of the active material in a lead-acid battery cell. However, in embodiments of the present invention, such "undesirable" volume changes are exploited in order to provide a useful feature: precise, controlled drug-delivery such as that required for slow-infusion or medical devices. A benefit is that this enables increased control over the delivery of liquid drugs via a programmable electronic system.

Embodiments of the present invention relate to an interesting demonstration of how physical changes that occur in batteries during discharge can be exploited for performing useful mechanical work. Conventional batteries are used to convert chemical energy into electrical energy. We report here on batteries where this conversion is instead optimized for supplying mechanical energy derived from large increases that occur in the volume of an anode, cathode, or both, as the cell is discharged. Such physical expansion of the anode, cathode, or both electrodes is expressed as increasing cell height in such cells sealed in an expandable housing. This axial expansion can add significantly to original height making them attractive as simple self-powered mechanical actuators for various devices. As such cells can be made with a range of initial heights, multi-millimeter expansions are achieved with generation of forces of more than 1 Kg/cm$^2$ per electrode cross-sectional area. Control of both the rate at which the height increases and the total expansion is accomplished by normal regulation of discharge.

In one example application, such battery cells compress a semi-flexible drug reservoir in a drug delivery pump pushing fluid into an attached tubing that delivers the medication for sub-cutaneous injection via a soft cannula. The pump can operate for several days. Dosing levels can be controlled from fast deliveries of several hours down to several tens of microliters per hour with high accuracy. The technology is designed to deliver drug volumes of 1 to about 10 cc which are in the range between that delivered by syringes and that of infusion drip bags.

Numerous types of inexpensive drug-delivery mechanisms are known, typically employing a gas-driven infusion principle. U.S. Pat. Nos. 5,318,557 and 5,527,288 describe an inexpensive, gas-driven infusion device which can be manufactured sufficiently inexpensively in order to constitute a disposable product. The embodiments described therein employ an electrolytic cell for gas production as per U.S. Pat. No. 5,062,834. A similar gas-driven device is described in U.S. Pat. No. 5,354,264. This device utilizes gas pressure from free oxygen and hydrogen derived from the electrolysis of water at the electrodes in negatively charged polymeric hydrogels. Said device ensures that the gas generated remains within the walls of the gas chamber by making said walls "rigid and impermeable to gases". In all these devices, the gas pressure forces the infusion of the drugs through appropriate means into the body, with the pressure being dependent on the rate of electrolysis, which is in turn controlled by an electric current. A further class of devices uses the same gas-driven principle, but generates this gas by chemical rather than electrical means. For example, U.S. Pat. No. 5,814,020, hereby incorporated by reference, describes a gas-powered infusion device where the gas is generated either by an electrolytic cell or by the reaction between citric acid and sodium bicarbonate; said reaction generating carbon dioxide and water.

The central problem with these gas-driven devices is that they all employ a gas-filled chamber in order to drive the drug infusion. As gases are very susceptible to changes in ambient temperature and air pressure, the danger of employing this principle is that a significant and undesirable change in the flow-rate will occur as such temperature or pressure changes occur. For example, a loss of pressure in an airplane could result in a sudden bolus being delivered at an inappropriate time. Similarly, a drop in temperature could result in the drug infusion stopping. For these reasons, despite massive development efforts, these products have faced considerable commercial obstacles to implementation. The literature confirms the problematic nature of this issue. In a partial attempt to address this issue, U.S. Pat. No. 6,186,982 describes a flow-regulation chamber appropriate to the above-described devices which attempts to compensate for such temperature and/or pressure changes. Nonetheless, this issue of heat and pressure sensitivity is an inherent disadvantage inhibiting the commercialization of these products. Additionally, even when the surrounding conditions are constant, these technologies suffer from the disadvantage of providing a time-lagged response to the control system. For example, if the system's control requires a complete halt of the drug delivery, the residual gas pressure will keep pushing the drug out.

Further known technology in this field includes (a) MEMS-based pumps in which a miniature pump is implemented on a silicon chip using integrated-circuit fabrication techniques, such as the Chronojet™ from Debiotech S. A. (Lausanne, Switzerland); (b) those in which a piezo-electric pumping mechanism is used such as U.S. Pat. No. 6,589,229; and (c) those which use SME wire technology such as the OmniPod™ product from Insulet, Inc. (Bedford, Mass., USA). All these approaches entail complicated mass-manufacturing issues, which have either not yet been solved or require elaborate control mechanisms and fine tolerances; both of which greatly increase costs to the point where it is difficult to produce a disposable product.

Another major concern with existing drug delivery devices is the difficulty of making such a complex mechanism (and its associated electronics) waterproof. This issue is tackled either by the users being very careful not to get it wet, or by a complex sealing of the mechanism package. Said sealing is inherently difficult with permanent pump devices where new disposable infusion sets need to be periodically attached to the device.

Accordingly, the achievement of a novel battery cell capable of a significant displacement (that is one capable of effectively driving a drug delivery device and herein referred to as a "displacement-generating battery") allows for a unique, beneficial, simpler and therefore more inexpensive solution for drug-delivery devices to be attained. Notably, such a drug-delivery device, in its simplest embodiment, would not require any mechanical or hydraulic amplification and thus would represent an advance in the art, as it would enable direct displacement of a drug in a reservoir within said drug-delivery device by said battery cell. In some embodiments of this invention the battery cell displaces a disc, plate, diaphragm, or piston as a coupling component located between the battery cell and the drug reservoir that in turn displaces a liquid drug in the reservoir within said drug-delivery device. In addition, since the displacement generated by the battery is directly related to the accumulated electric discharge in the battery, the extent of the displacement of a drug in a reservoir can be very accurately controlled.

Accordingly, there is a need for an inexpensive drug-delivery device which is capable of very precise actions while only requiring low manufacturing tolerances, and is simple to operate with minimal requirements for internal control/feedback mechanisms.

It is still further object of embodiments of the present invention to provide a drug-delivery device whose delivery rate and volume of drug delivered is accurately controlled by an electrochemical reaction, and specifically, by an electrochemical reaction that causes a volume or shape change that actuates the delivery of the drug. In a preferred embodiment the volume change is positive, that is, the displacement is positive.

It is still further object of embodiments of the present invention to provide a displacement-generating battery that is used as an actuator which transmits a displacement resulting from an electrochemical reaction via a coupling component in such a manner that a drug contained within a drug reservoir affected by the coupling is forced through an administration means into the body of a patient.

It is also the object of embodiments of the present invention to provide a drug-delivery device which is relatively insensitive to temperature and pressure changes.

It is a further object of embodiments of the present invention to provide a drug-delivery device where the energy derived from the discharge of said battery provides the main power source for said delivery.

It is a still further object of embodiments of the present invention to provide a drug-delivery device with a minimum of moving parts.

It is a still further object of embodiments of the present invention to provide a drug-delivery device with inherent position determination. In one embodiment of the present invention the inherent position determination is achieved via a Hall sensor and a magnet, where the distance between them varies with the displacement thereby causing changes in the detected magnetic field that can be sensed by the drug-delivery device.

It is a still further object of embodiments of the present invention to provide a drug-delivery device which does not suffer from an unacceptable lag in response time.

It is a still further object of embodiments of the present invention to provide a drug-delivery device which is inherently waterproof.

It is a still further object of embodiments of the present invention to provide a drug-delivery device where control and maintenance issues are simpler than in existing approaches and with less potential failure modes.

It is a still further object of embodiments of the present invention to provide a drug-delivery device in which the displacement-generating battery also provides the power to operate the electronics of the device thus advantageously obviating the need for having a further battery cell to power the electronics of the drug-delivery device and so the device is simplified, made more efficient, and lowered in cost.

These and other objects of embodiments of the present invention will become more evident in the summary of the invention and in the description of the preferred embodiment.

BRIEF SUMMARY OF THE INVENTION

According to embodiments of the present invention there is now provided a delivery device for drugs or other substances (henceforth a "drug-delivery device") comprising a drug reservoir chamber containing a substance to be delivered, in fluid connection with a drug administration means, and at least one displacement-generating battery cell coupled to said drug reservoir chamber by a coupling means, the at least one displacement-generating battery cell comprising at least one element that changes shape as a result of discharge of the battery cell so as to cause a displacement within the battery unit, the arrangement being such that the displacement derived from said battery unit is conveyed by said coupling means to cause displacement of at least a portion of a wall of said drug reservoir chamber reducing the volume of said drug reservoir chamber such that said substance is expelled from said drug reservoir chamber towards said drug administration means upon discharge, thereby being a self-powered drug delivery device.

In some embodiments, the invention provides a self-powered drug-delivery device comprising a drug reservoir chamber having a wall, containing a substance to be delivered, in fluid connection with a drug administration means, and an electrically-controlled battery unit comprising at least one displacement-generating battery cell coupled to said drug reservoir chamber by a coupling means, the at least one displacement-generating battery cell comprising an element that changes shape as a result of discharge of the battery cell so as to cause a displacement within the battery unit, the arrangement being such that the displacement derived from said battery unit is conveyed by said coupling means to cause displacement of the wall of said drug reservoir chamber reducing the volume of said drug reservoir chamber such that said substance is expelled from said drug reservoir chamber towards said drug administration means upon discharge, thereby being a self-powered drug delivery device.

In some embodiments of the present invention the coupling means involves a displaceable wall of the drug chamber applying direct or indirect displacement from the battery unit to the drug chamber.

In some embodiments of the present invention the coupling means is a common wall of the battery cell and the drug reservoir.

In further preferred embodiments of the present invention, the coupling means involves a displaceable wall applying indirect displacement from said battery unit to said drug chamber. In some embodiments, the phrase "indirect displacement" is meant to relate to the existence of movable parts within the device, which relay the displacement effected by the battery cell. Some examples, according to this aspect, include a piston, diaphragm, or plate element incorporated within the device and operationally connected on one front to the battery cell and on another front to the drug reservoir. Some examples, according to this aspect, include displacement of the piston, diaphragm, or plate element, which in turn causes displacement of at least a portion of the drug chamber operationally connected thereto.

In one embodiment, the devices of this invention comprise a coupling means external to the battery cell and such coupling means, in some embodiments, is hydraulic. In other embodiments, such coupling means is mechanical.

In some embodiments, the battery cell shape change is a result of at least a partial volume expansion in the battery cell. In some embodiments at least one electrode in the battery cell undergoes at least a partial volume change. In some embodiments, only one electrode of an electrode pair in the battery cell undergoes at least a partial volume change.

Thus according to one embodiment of the present invention there is provided a delivery device for drugs or other substances (herein a "drug-delivery device") comprising a drug reservoir chamber having at least one displaceable wall and containing a substance to be delivered in fluid connection with a drug administration means, and a displacement-generating element, the element being an electric battery unit comprising at least one displacement generating battery cells coupled to the drug chamber by a coupling means, the arrangement being such that a change in the volume or shape of at least one component of the electrochemistry of the battery unit (during discharge of the displacement-generating battery) causes a wall or a portion thereof of the battery unit to be displaced, which in return causes a wall or a portion thereof of said drug chamber to be displaced such that the substance is expelled from the drug chamber towards the drug administration means.

In some embodiments of the present invention the drug administration means is selected from the group consisting of cannulas, cannula arrays, needles, needle arrays, exit ports and transdermal patches. These means may be part of an infusion set connected to the drug delivery device via an interface or an insertion mechanism integrated into the drug delivery device.

Preferably the volume of each of the at least one displacement-generating battery cells is changed as its respective electrical capacity is changed.

In some embodiments the combined volume of electrodes and electrolyte within the battery cell changes its volume as its electrical charge is depleted on application of a load across the electrical contacts. In some embodiments, the volume or shape of an electrode or a portion thereof changes as the electrical charge is depleted.

In some embodiments, a battery cell shape change is a result of discharge of the battery. In some embodiments, at least one electrode in the battery cell undergoes volume expansion. In some embodiments, only one electrode of an electrode pair in said battery cell undergoes volume expansion or shape change.

In some embodiments the drug-delivery device may be employed in a number of different configurations, including but not limited to: implantable devices, slow-infusion devices, disposable infusion devices, partially-disposable infusion devices and patch-pumps attached to the skin for sub-cutaneous or arterial or venous delivery. Such drug delivery devices are useful for delivering drugs to patients which may be humans or other animals. Given the absence of motors and other such sensitive components, the drug-delivery device of the present invention can conveniently be rendered waterproof.

The displacement-generating battery used in the device may be either a primary cell or a secondary cell, or involve more than one cell. Where a primary cell is used, the volume or shape change is caused by its discharge, and where a secondary cell is used, the volume or shape change may be effected during either the charging or discharging thereof. In either case, such a displacement-generating battery is hereby defined as one in which at least one component of the battery cell undergoes at least a partial volume or shape change producing a displacement of at least 20% or preferably at least 30%, as opposed to conventional batteries which are designed so that volume changes are minimized to substantially lower values. This volume or shape change is then conveyed directly or via a coupling component to a displaceable wall of the drug chamber, causing the drug therein to be delivered via the administration means.

In some embodiments, the drug reservoir chamber has a semi-rigid structure, which can be viewed as a displaceable wall. In some embodiments the drug reservoir consists of two portions sealed together, one portion being rigid and the other semi-rigid or displaceable. The two portions may be of the same material or different materials. The semi-rigid and displaceable elements may be a blister, film, or membrane of a suitable polymer as a single layer or a multi-layered structure of at least two layers of different polymers and tie layers. The rigid portion may be shaped similar to a lens or dome. Sealing of the two portions may be via heating, thermal processes, impulse welding, ultra-sonic, and the like.

In some embodiments, the displaceable wall of the drug chamber can take a number of forms, including but not limited to: a rigid yet displaceable section of the wall, a flexible or bellows type wall section, a liquid-liquid interface and a piston. A simple example of a chamber with a displaceable wall is a cylindrical cell with a rigid circular cap sealed against one end by means of an elastomeric gasket, the cap being capable of moving up or down as the discharge of the displacement-generating battery proceeds.

In many cases, the displaceable section of the wall of the drug chamber moves in response to the displacement of the displacement-generating battery. In a drug-delivery device embodiment of the present invention the movement of the displaceable section serves to expel a drug from a drug chamber via a channel in the drug chamber to an administration means into the body of a patient. In the case where the displaceable section is a semi-rigid blister, film, or membrane, in one embodiment the displacement of this section causes the semi-rigid element to move into the cavity of the drug chamber in a way that its peripheral edge folds or rolls against the perimeter of the rigid portion of the drug chamber. The material for the ridged base plate may be cyclic olefin polymer (COP). The material for the blister or film may be COP. A COP base plate may be welded to a COP blister, film or membrane.

In a preferred embodiment of the present invention, the displacement-generating battery employed within the present invention applies direct displacement to a drug chamber wall, such that the drug contained within the drug chamber is forced through an administration means into the body of a patient. In a further preferred embodiment of the present invention, the displacement-generating battery applies direct force to a wall of a pouch or other envelope comprising the at least partially flexible or displaceable walls of the drug chamber, such that the drug contained within the drug chamber is forced through an administration means into the body of a patient.

In one embodiment, the displacement-generating battery employed within the present invention pushes a piston of a drug chamber (either directly or via mechanical or hydraulic coupling) such that the drug contained within the drug chamber is forced through an administration means into the body of a patient. The administration means can include a conventional cannula as known in the art, or any other means whereby the drug is introduced into the body. Such means can include arrays of short cannulas such as the SimpleChoice™ patch product (SpectRx, Inc., Norcross, Ga., USA), arrays of micro-needles, non-invasive transdermal devices, or auto needle insertion means. Alternatively, where a drug-delivery device embodiment of the present invention is an implantable one, the delivery means can be any exit port or tube leading from the device to the required location in the body of the patient.

In some embodiments, at least one component of the device, such as but not limited to a battery or battery cell, undergoes a volume or shape change causing a displacement in excess of 20% and preferably in excess of 30% of its initial volume or shape, during discharge.

In some cases, the overall change in volume or shape of the entire battery or battery cell is smaller than this amount (as one element of it shrinks or is depleted while another grows), but this is not important providing that it is still possible to mechanically exploit the volume-changing or shape-changing of the complete component by mechanically supporting the displacement-generating component while ensuring that the cell casing as a whole does not collapse or cause any other structural problem.

In this manner, the full displacement of the displacement-generating element of the component—in this case an electrode or a portion thereof, or a single electrode in an electrode pair—may be exploited.

In some cases, such electrodes will benefit from a larger surface area, i.e. thinner sections and larger internal surface area, for example those achieved by using a pressed, pasted or sintered porous structure or one based on finer particles. This will allow easier access of ions for intercalation and enable higher rate discharges. In the case of a displacement-generating battery, not only is the degree of expansion important, but also the force developed should be adequate for drug-delivery. Internal stresses in the expanding electrode of at about 1 kg/sq cm and much higher should be attainable in the course of discharge or charge.

In some embodiments the battery cell is selected from the group consisting of a lead-acid battery, a dry cell battery, an alkaline battery, a nickel-cadmium battery, a lithium ion battery and a fuel cell The alkaline battery includes a group of battery chemistries that includes those dependent on the reaction of zinc-manganese dioxide and which contain electrolyte that includes either KOH, NaOH, or combinations of them, zinc-silver oxide system, and zinc-air systems. A preferred chemistry is the alkaline zinc-manganese dioxide battery system.

Zinc anodes can be used in cells with various electrolytes, and significant zinc expansion occurs in alkaline electrolyte systems. For example, embodiments of the present invention encompass the use of aqueous KOH, with a concentration of, for example, 28-50 weight percent. The electrolyte may contain some additives chosen from the group that includes zinc oxide, and other metal oxides. In acidic and neutral electrolytes the zinc discharge product is soluble in the aqueous solution (leaving a void or negative volume change at the anode side of the cell). Thus alkaline electrolyte battery systems are particularly suitable for consideration for embodiments of the present invention.

Zinc-manganese dioxide is a safe battery system widely used by consumers since the early 1960s. They are safe, non-toxic and can be disposed of by the consumer preferably at battery recycling points. The alkaline zinc-manganese dioxide cells are benign enough so the US DOT and EPA do not regulate their transport.

In the alkaline zinc-manganese dioxide cells both the zinc and the cathode expand, according to embodiments of the present invention. The expansion of the zinc can reach 100% of the initial electrode height, and in some embodiments about 135%. The $MnO_2$ cathode according to some embodiments can expand to about 60% and in some embodiments about 75%. The zinc anode can account for the majority of the cell expansion.

Zinc anodes in aqueous alkaline cells react during cell discharge to form a new compound, zinc oxide. The theoretical volumetric change based on molar volumes of zinc and zinc oxide 58%. According to embodiments of the present invention, greater expansions are achieved since the zinc expansion is constrained to only the vertical direction, there is abundant electrolyte quantity that is thought to shift the reaction pathway to different morphology zinc oxide and affects the solubility and precipitation of the zinc oxide derived from the discharge reaction, and the anode structure (porosity, compression, particle size, etc.) is adjusted for achieving maximum vertical expansion of even around 135%.

At the cathode in a preferred embodiment, the expansion is also confined to just the vertical direction, there is an abundant quantity of alkaline electrolyte in the cell which is thought to affect the reaction pathway, and the cathode structure (porosity, compression, particle size, and the like) is adjusted for achieving maximum vertical expansion. Thus, while for some reaction pathways the $MnO_2$ cathode discharges with a theoretical expansion of 17%, in a preferred embodiment the expansion can reach much higher values of around 75%.

As a combined electrode system in a preferred embodiment battery cell, and taking into account housing and electrolyte, overall cell vertical expansions of preferred embodiments can reach about 50% increase above the original cell height, and generate forces of about 1 Kg/cm² or more per electrode cross-sectional area.

The electrochemical reaction of the zinc anode in alkaline electrolyte converts zinc metal into zinc oxide as:

$$Zn+2OH^- \rightarrow ZnO+H_2O+2\ e^-$$

Since the zinc oxide product is only slightly soluble in the electrolyte it accumulates at the anode taking the place of the consumed zinc. The small solubility of the zinc oxide in the alkaline electrolyte can be handled by preparing the electrolyte with ZnO. This encourages a high conversion efficiency during discharge to solid ZnO so that much of the zinc oxide that is produced contributes to the expansion of the electrode. The ZnO precipitates out of solution to form a hard solid at the anode and this product is sometimes referred to 'hard' zinc.

The zinc used in the alkaline electrolyte cells is typically in the form of a compressed powder. In order to minimize the tendency of the zinc to corrode in aqueous electrolytes various inhibitors either mixed with the zinc or as additives to the electrolyte may be used to reduce gassing. Relatively small amounts of various additives chosen from a group that includes metal or metal compounds of bismuth, lead, indium separately or in combination are present with the zinc powder and can possibly alloy with it.

Manganese-dioxide is a preferred cathode chemistry to couple with the zinc in a volume changing battery cell.

The basic electrochemistry of the zinc-manganese dioxide system has been well studied and characterized. The basic features are presented below.

During cell discharge the oxygen rich manganese dioxide cathode is reduced while the zinc is oxidized to form zinc oxide. Water is consumed in the cell reaction. The cell reaction can be represented as:

Battery Reactions.

Positive reaction: $MnO_2+H^+e^- \rightarrow MnOOH$ negative reaction: $Zn+2OH^- \rightarrow ZnO+H_2O+2e^-$ total reaction: $2MnO_2+H_2O+Zn \rightarrow 2MnOOH+ZnO$ The open circuit voltage of the cell is about 1.6 volts. The alkaline electrolyte of potassium hydroxide is not consumed during discharge.

The cathodic half-reaction may also proceed to some extent via the reaction $$2MnO_{2(s)}+H_2O_{(l)}+2e^- \rightarrow Mn_2O_{3(s)}+2OH^-_{(aq)}$$

The cathode is a mixture of electrolytic manganese dioxide, and a conductive carbon like acetylene black or more usually graphite, and preferably highly crystalline graphite. In some embodiments a binder is also used. Electrolyte solution may also be added to help form the cathode mix. According to some embodiments, an electrolytic type manganese dioxide is used. It is understood that chemical or natural types can also be used. Typical binders include items from a group that includes polymers and co-polymers of polyethylene, high density polyethylene, low density polyethylene, polypropylene, polyvinylidene fluoride (PVDF), polyacrylic acid (PAA), potassium titanates fibers, calcium silicate fibers, and polytetrafluoroethylene (PTFE) and similar fluorinated polymers. Typical compositions are 80-90% MnO2, 5-10% conductive additive, and 5-10% electrolyte.

The separators can be chosen from a group that includes polypropylene non-woven material, microporous polypropylene, monolayer polypropylene (PP), monolayer polyethylene (PE), and trilayer PP/PE/PP, microporous polyethylene, and other non-woven separators made from materials such as cellulose, cellophane, Nylon, polyvinyl acetate (PVA) and other fibrous materials. The separators may be coated with surfactants. The separators may also be of the laminated type.

Anode casings or current collectors (e.g. cups) can be chosen from a group that includes zinc, brass, copper, titanium, tungsten, tantalum, and such metals that are either cladded or coated with other metals from a group that includes indium, zinc, lead, bismuth, and others. The metal anode casings can be made as an over-mold of a suitable polymer like polyethylene (PE), polypropylene (PP), polyvinyl chloride (PVC), or one of the members of the Bondyram® family from Polyram Ltd., Israel. Bondyram polymers are based on maleic anhydride modified polyethylene or polypropylene. Bondyram polymers can also be used as coupling agents, as a sort of adhesive or adhesive promoter, between the metal anode case and the overmold polymer. One benefit of the overmolded metal anode case is that it can be made of the same polymer as the cell housing in order to weld them together.

The cathode casing or current collector can be chosen from a group that includes steel, stainless steel, nickel, and such metals that are cladded (bi or tri) or coated with nickel. The anode and cathode casings can also be chosen from a group that includes polymers that include Ultem, polyetheretherketone (PEEK), acrylonitrile butadiene styrene (ABS), polypropylene (PP), high density polyethylene (HDPE), low density polyethylene (LDPE), nylon, polystyrene, with a metal disc or contact pin or collector.

The cells may be housed in at least partially flexible film housing that can be chosen from a group that includes a monolayer of polypropylene (PP), PE (low or high density), polyvinyl chloride (PVC), and at least a bilayer of these materials produced via lamination, co-extrusion, or coating with an oxidation and/or evaporation barrier chosen from a group that includes polyethylene terephthalate (PET), polyamide (nylon), ethylene vinyl alcohol (EVOH), cast polypropylene (CPP), and others. The bilayer may be for instance cast polypropylene/polyamide (CPP/PA).

In some embodiments the battery cell further comprises an internal gas volume which is consumed by a chemical reaction within the battery cell taking place on discharge of the battery cell.

In especially preferred embodiments of the present invention at least one displacement-generating battery cells employs a chemical reaction system based on electrochemical insertion of metal ions.

Preferably each of the at least one displacement-generating battery cells employs a chemical reaction system chosen from the group including Li—Sn, (Li)LiC$_6$—Sn, Fe—LaNi$_5$, lithium-lead, lithium-antimony, lithium-silicon and lithium-bismuth.

Preferred electrochemical systems for the displacement-generating battery that employs a chemical reaction system based on electrochemical insertion of metal ions include but are not limited to Li—Sn and (Li)LiC$_6$—Sn; both of which are based on the phenomenon of the increase of thickness (up to 257%) of a tin (Sn) electrode under the chemical reaction with (or electrochemical intercalation of) Li ions. A third system, Fe—LaNi$_5$ (basically, a kind of a metal-hydride battery), could be used due to the expansion of the Fe electrode (estimated as 250%) during its oxidation to FeOOH. Further candidates for anodes include alloys of lithium such as (but not limited to) lithium-aluminum, lithium-magnesium, lithium-aluminum-magnesium. According to some embodiments of the present invention, various other displacement-generating battery chemistries can be chosen for the battery cell, subject only to certain volume-changing or shape-changing requirements discussed elsewhere herein. According to some embodiments, further candidates for battery systems include lithium-lead, lithium-antimony, lithium-silicon, lithium-bismuth and fuel cells; providing that they achieve the volume-changing or shape-changing requirements discussed elsewhere herein. In the case of fuel cell batteries, the volume depletion of the fuel provides the volume-changing or shape-changing element.

Lithium based batteries use organic solvents or a polymer electrolyte together with a lithium ion-providing salt. Suitable non-limiting examples of such organic solvents include propylene carbonate, tetrahydrofuran, 2-methyl tetrahydrofuran, gamma-butrolactone, ethylene carbonate, dimethoxy ethane, dioxolane, diethyl carbonate, dimethyl carbonate, ethylmethyl carbonate, and various combinations of such solvents. Suitable non-limiting examples of electrolyte salts for such organic solvents include lithium perchlorate, lithium hexafluoroaresenate, lithium hexafluorophosphae, lithium tertrfluoroborate, LiCF$_3$SO$_3$, and LiN(CF$_3$SO$_2$)$_2$. Generally, as the discharge or charge proceeds in such systems, there is either a net volume or shape change of the system or a large volume or shape change in at least one electrode. Variations on the above systems may use lithium-carbon, lithium-graphite or lithium-aluminum alloys in place of the lithium electrode. An example of an electrolyte for the lithium-tin system is a solvent of a mixture of ethylene carbonate and ethyl methyl carbonate with dissolved lithium hexafluorophosphate as the ion-providing (ionizing) salt. Other lithium ion conducting electrolyte types are applicable, such as gel, polymer or solid state electrolytes. The basic volume or shape change in these systems occurs as a result of lithium ion intercalation from the lithium electrode into the other electrode during the electrochemical reaction, which is driven by the potential difference between the electrodes. In the case of a lithium-tin battery, the tin electrode can expand by up to 257% in volume during discharge, while generating stresses of 15 kg/sq cm. This electrode expansion can be understood by comparing the densities of lithium (0.53) and tin (7.3). Where the electrochemical reaction within the displacement-generating battery is a reversible one, a battery cell of this type can also allow refilling of the drug-delivery device.

This approach to drug-delivery device design has a number of advantages. As there is no pump or motor in the conventional sense, there are very few parts, and in exemplary embodiments only a coupling component such as a displaceable wall between the cell and the drug chamber is a moving part. By using a minimum number of moving parts, failure modes and maintenance issues are minimized. Additionally, factors such as noise, friction, backlash and assembly tolerance issues are minimized. Accordingly, very precise control of the drug-delivery device is enabled by this design. In fact, providing that the non-displaceable walls of the battery remain rigid, the resolution of the achievable movement is limited only by the accuracy of the charge/discharge circuitry; something which can be provided to a very high degree using electronic circuitry known in the art. This is especially important in the case of implantable drug-delivery devices, where drug-delivery rates in the picoliter range per minute are required so as to be able to deliver drug quantities in the milliliter range over a period of months or years. Additionally, advantageously this approach provides the ability to determine the volume of drug delivered, purely by integrating the electric charge (that is, the current per unit time) used during charge or discharge of the battery. According to some embodiments, it is possible to further provide (a) a closed-loop or feedback control where which incorporates position-detection elements such that the information concerning the volume of drug delivered is not solely dependent on monitoring the charge/discharge performed; and (b) pressure sensors and other feedback and safety means can be incorporated into the control circuitry and logic.

One preferred closed-loop position control system includes a magnet and a Hall effect sensor or a plurality of magnets associated individually with a plurality of Hall sensors.

In one embodiment the Hall sensor portion of the system is on the opposite side of the volume displacing cell than the magnet. For example, the Hall sensor is located on the printed circuit board and the magnet part of the system is located on the other side of the volume displacing battery, for example either residing on the cell between it and the piston or attached to the piston. The location of the magnet and Hall sensor can be exchanged in this embodiment. In another example of this embodiment the magnet may be located in the volume displacing cell itself.

In another different embodiment, the Hall sensor and the magnet components of the closed-loop position system are located on the same side of the volume displacing cell that faces the drug reservoir. In one example the Hall sensor portion of the system is attached to the piston, or sits between the piston and the volume changing cell, and the magnet portion of the system is situated on the opposite side of the drug chamber from the piston, for example in the pump housing or between the pump housing and the drug reservoir. The location of the magnet and Hall sensor can be exchanged in this embodiment. In yet another version of this embodiment, the magnet resides in the volume displacing cell and the Hall sensor resides on the opposite side of the drug chamber from the piston, for example in the pump housing or between the pump housing and the drug reservoir.

In these embodiments of the closed-loop position control center it is important that the Hall sensor and the magnet be aligned. The magnet may be of any type including neodymium (Nd) type magnets.

In one embodiment the pressure sensor is a force sensing resistor (FSR). Typically it is made of a polymer film ink printed onto a substrate such as polyethylene terephthalate (PET). As force is applied to the FSR the electrical resistance decreases and this is sensed by the electronics of the pump. A test square resistance after a second hit is typically around 95 kohms+/−20%. The ink thickness is typically around 0.01 mm, but can be adjusted as per the application. An adhesive may be applied to the FSR to attach it to various surfaces. The FSR may have a hole in the center so that either the magnet or the Hall sensor of the closed-loop position control system may be located within it, or some other component.

In some embodiments the battery cell serves to power at least some of the electrical and electronic elements of the device. In some embodiments the drug-delivery device is disposable. In some embodiments the drug-delivery device is partly disposable. In some embodiments the drug-delivery device is an implantable device. In further embodiments the drug-delivery device further comprises a filling means. In some embodiments the drug-delivery device further comprises a battery recharging means. In some embodiments, the drug-delivery device is a multiple-use device.

In some embodiments of the present invention the drug-delivery device is a patch-type pump, and preferably the patch-type pump is attached to the body by a means comprising an adhesion means, a strap, a clasp and combinations thereof.

In other embodiments of the present invention said drug-delivery device further comprises an auto-insertion means, and preferably said auto-insertion means serves to insert the administration means.

In other embodiments, the auto-insertion means automatically activates the drug-infusion device. The activation in an embodiment could be via a Reed switch situated in the pump and an activating magnet located in the auto-insertion means.

In further embodiments of the present invention the drug-delivery mechanism further comprises a plurality of drug chambers, and preferably the drug-delivery device includes means for the mixing of the drugs from the plurality of drug chambers.

In other embodiments of the present invention the drug-delivery device further comprises a plurality of control cells.

In some embodiments of the present invention the drug chamber includes means enabling the intake of body fluids; the fluids serving to dilute a drug for subsequent administration by the drug-delivery device on reversion to its normal operating mode.

In some embodiments, the device further comprises means for sampling body fluids for analysis.

In some embodiments of the present invention the drug-delivery device further comprises communications means to remote devices selected from the group consisting of magnetic induction, infra-red, and RF devices.

Preferably the administration means further comprises a safety feature to protect against accidental contact or injury.

In some embodiments of the present invention the change of volume or shape of the drug chamber is proportional to the change in the volume or shape of the control chamber.

Preferably the change in the volume or shape of the volume changing means is proportional to an external non-gas evolving electric perturbation.

In one embodiment of the present invention the drug reservoir chamber is coupled to said hydraulic control chamber via a displaceable wall; such that the volume or shape change of the volume-changing or shape-changing means serves to control the rate of delivery of the drug.

Preferably the drug reservoir chamber is coupled to the hydraulic control chamber via a piston arrangement; such that the volume or shape change of the volume-changing or shape-changing means serves to control the rate of delivery of the drug.

In some embodiments, the drug-delivery device of the present invention utilizes an electrochemical volume-changing or shape-changing means, wherein a number of electrochemical reaction systems are considered. They include but are not limited to:

1. The lead-acid reaction: $Pb+PbO_2+2H_2SO_4=2PbSO_4+2H_2O$ whereby one gm mole of reactants 642 gm (154 cc) contracts on discharge by 13%. In this system the positive electrode is lead dioxide, the negative electrode is lead and the electrolyte is sulfuric acid. Discharge to the reaction products (in this case lead sulfate and sulfuric acid further diluted with water) which have different densities and molecular weights from the starting materials, causes the net volume contraction or shape change.

2. The nickel-cadmium cell reaction: $Cd+2NiOOH+2H_2O=Cd(OH)_2+2Ni(OH)_2$ in which one gm mole of reactants 332 gm (90 cc) contracts on discharge by 15%.

3. The dry cell reaction: $Zn+2MnO_2=ZnO+Mn_2O_3$ whereby one gm mole of reactants 239 gm (44 cc) expands on discharge by 13%.

4. The formate/$MnO_2$ fuel cell: $HCOOK+2MnO_2+KOH=K_2CO_3+2MnOOH$ whereby one gm mole of reactants 314 gm (106 cc) contracts on discharge by 8%. In this case the negative electrode is an aqueous solution of potassium formate "fuel" in contact with a catalytic electrode, the positive electrode is manganese dioxide and the electrolyte is aqueous potassium hydroxide. The fuel gaseous oxidation product, carbon dioxide, reacts in-situ with the alkaline electrolyte, forming liquid phase potassium carbonate.

5. The Zinc-Manganese dioxide battery chemical reaction: $2MnO_2+H_2O+Zn \rightarrow 2MnOOH+ZnO$ whereby the expansion of the manganese tablet from $MnO_2$ to $MnOOH$ is typically of the order of 50%. Given a ratio of initial heights of 1:5 between the zinc and manganese tablets, the resulting overall expansion of the battery cell is thus of the order of 50% relative to the initial height.

Alternatively, the volume-changing or shape-changing means may be a solid-state one such as a lithium-ion type battery or an electroactive polymer such as those described in IEEE Spectrum Online ("Electric Flex"), June 2004 (http://www.spectrum.ieee.org/WEBONLY/publicfeature/jun04/0604art.html), the content of which is incorporated herein by reference.

In either case, where the volume-changing or shape-changing process is a reversible one, then such a control cell can also allow refilling of drug-delivery device embodiments of the present invention, which can be an important feature for implantable devices.

This approach to drug-delivery device design has a number of advantages. As there is no pump or motor in the conventional sense, there are very few parts, and in many instances only the piston or other displaceable wall is a moving part. By using a minimum number of moving parts, failure modes and maintenance issues are minimized. Additionally, noise factors such as friction, backlash and assembly tolerance issues are minimized. Accordingly, very precise control of the drug-delivery device is enabled by this design. In fact, providing that the non-displaceable walls of the control cell remain rigid, the resolution of the achievable movement is limited only by the accuracy of the power supply and discharge circuitry; something which can be provided to a very high degree using electronic circuitry known in the art. This is especially important in the case of implantable drug-delivery devices, where drug delivery rates in the picoliter range are required so as to be able to deliver drug quantities in the milliliter range over a period of months or years. Additionally, advantageously this approach provides the ability to determine the volume of drug delivered, purely by knowing the electric charge/discharge performed. Despite this, according to some embodiments, it is possible to further provide (a) a feedback or control circuit which incorporates position-detection elements such that the information concerning the volume of drug delivered is not solely dependent on monitoring the charge/discharge performed; and (b) pressure sensors and other feedback and safety means can be incorporated into said control circuitry and logic.

Aspects of the present invention will now be described in connection with certain preferred embodiments, with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

BRIEF DESCRIPTION OF THE DRAWINGS

Embodiments of the present invention are herein described, by way of example only, with reference to the accompanying drawings, as follows.

FIGS. 3A and 3B provide block diagrams of further preferred embodiments of a drug-delivery device, further comprising a spring, FIG. 4 provides a block diagram showing the use of two control cells and the delivery of two-way motion.

FIGS. 7A to 7D provide isometric and cross-sectional figures showing preferred miniature embodiments of a drug-delivery device.

FIGS. 8A to 8E provide isometric and cross-sectional figures showing preferred embodiments of a drug-delivery device employing dual control cells.

FIGS. 13A to 13E show isometric and cross-sectional views of additional preferred embodiments of the drug-delivery device, including one in the form of a pen and one in which there is hydraulic coupling between the battery cell and the drug chamber.

FIGS. 14A to 14F provide an exemplary device, highlighting a displacement-generating battery cell according to embodiments of the present invention, showing an expansion of a Zinc-Manganese dioxide battery during charge depletion.

FIG. 16 shows aspects of an exemplary drug-delivery device according to embodiments of the present invention;

FIG. 18 shows aspects of an exemplary drug-delivery device according to embodiments of the present invention;

FIG. 20 shows aspects of an exemplary drug-delivery device according to embodiments of the present invention;

FIG. 21 shows aspects of an exemplary drug-delivery device according to embodiments of the present invention;

FIG. 22 shows aspects of an exemplary drug-delivery device according to embodiments of the present invention.

DETAILED DESCRIPTION OF THE INVENTION

Figure 1:
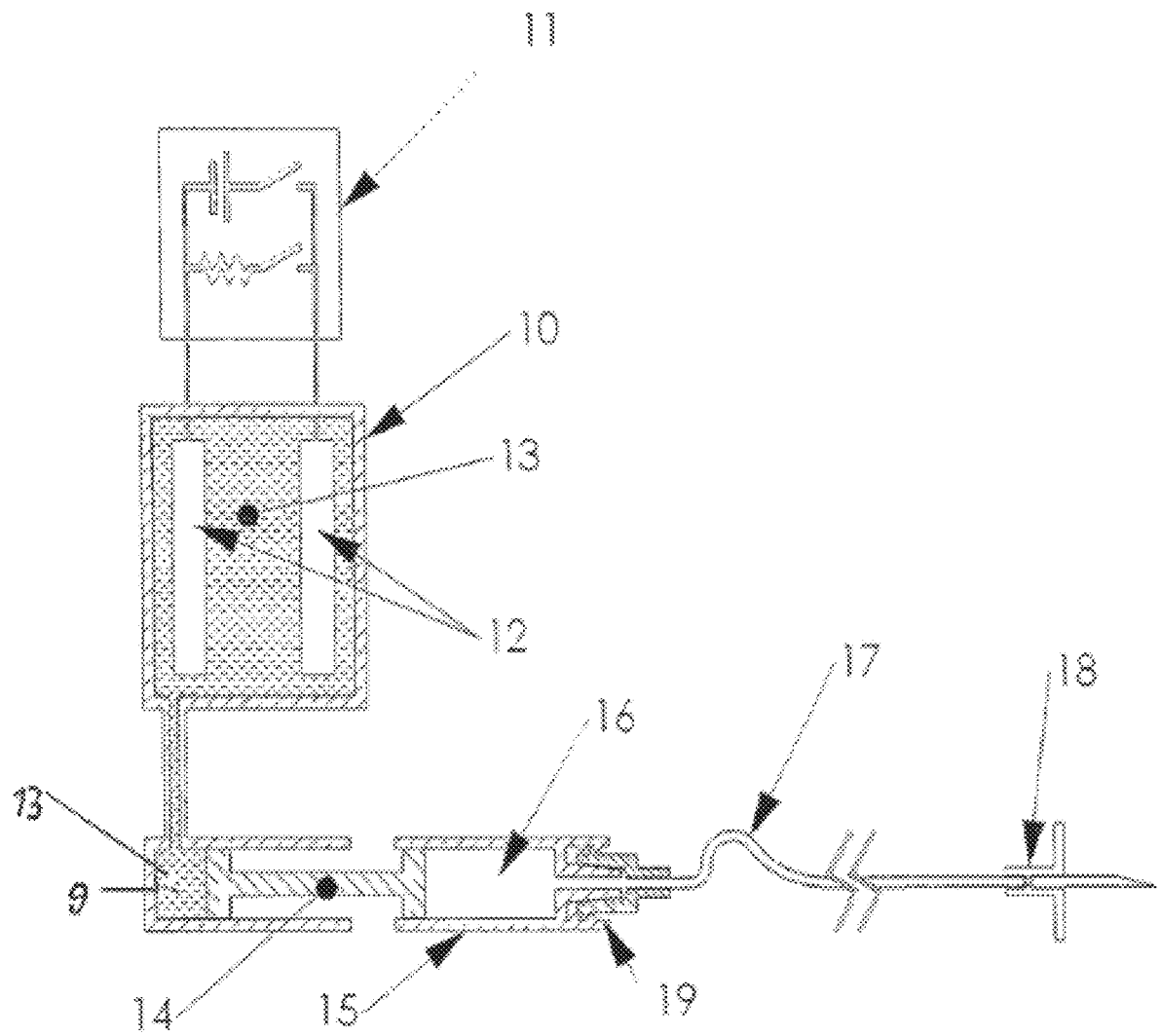
FIG. 1 provides a block diagram of an overall drug-delivery device, showing its main components, according to embodiments of the present invention.

The present invention will be described in detail according to the preferred embodiments illustrated in the accompanying drawings. Like reference numerals are used to identify identical components in the various views.

Referring to FIG. 1, a simplified block diagram of the drug-delivery device of the present invention is shown in its simplest configuration where an electrochemical control cell constitutes the volume- or shape-changing means. In this embodiment an electrochemical cell 10 which undergoes a volume increase on charging is charged via an electrical or electronic control circuit 11. Said circuit 11 can serve to either provide a charge to, or enable a discharge from, the cell 10; and for this reason both a battery and a resistor are shown within the block diagram of said circuit 11 for a schematic representation of its functionality. In the example shown, the battery within the circuit 11 in connected via contacts to the electrodes 12 and serves to charge the cell 10, such that the combined volume of the electrodes 12 and electrolytes 13 increases. The device includes hydraulic control chamber 9 which is in fluid connected with cell 10 and which therefore also contains the non-gas evolving volume changing or shape changing means which are electrolytes 13. As the only displaceable wall in the cell 10 and its connected hydraulic control chamber 9 is the piston 14, said piston 14 is forced into the drug chamber 15, causing the drug 16 contained therein to be expelled along the conduit 17 to a cannula 18 or other administration means. The administration means can be an integrated continuation of the drug chamber or a separated assembly introduced to the drug cell port through a custom connector or a standard connector such as Lauer Lock connector 19. As will be clear to one skilled in the art, the administration means can be any means whereby the drug or other substance delivered by the device enters the patient's body, including but not limited to an exit port in an implantable version of the device, and a cannula or cannula array or a transdermal patch for an external device.

Figure 2A:
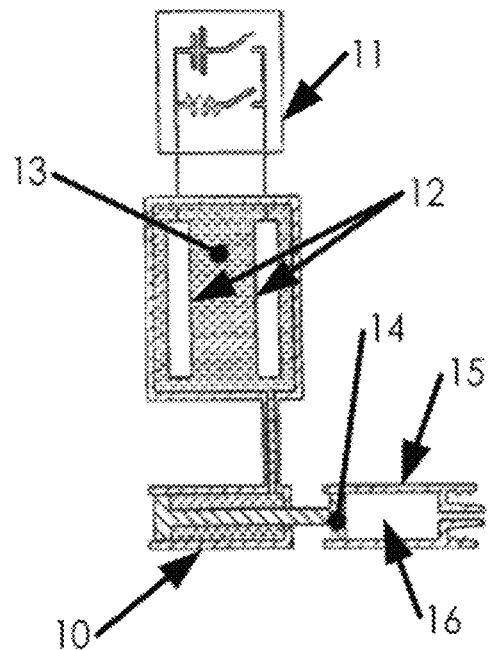
FIGS. 2A to 2D provides a block diagrams of preferred embodiments of a drug-delivery device showing different coupling arrangements between a drug chamber and a control cell.

Referring now to FIG. 2A, a preferred embodiment of the drug-delivery device of the present invention is shown. In this preferred embodiment, the electrochemical or control cell 10 is a battery cell and the primary function of the electric circuit 11 is to perform a controlled discharge of said cell. Advantageously, this embodiment obviates the requirement for a separate battery to drive the drug-delivery device, as the cell producing the volume or shape change is itself the battery. This provides a saving in the parts count, which in turn reduces the cost and weight of the device. Although there are battery cells (such as dry cells) which experience an increase of volume as they are discharged, in this preferred embodiment, the volume within the cell 10 decreases as it is discharged. Thus in this preferred embodiment the electronic control unit 11 serves to discharge the cell 10 such that the combined volume of the electrodes 12 and electrolyte 13 contracts. As this contraction occurs, the piston 14 advances into the drug cell 15, causing the drug 16 to be expelled. In this embodiment, the cell 10 is filled with either liquid or gel 13, where the electrode plates 12 serve to complete the battery system and this liquid or gel 13 serves to pull the piston 14 forward into the drug cell 15. The connection between the two cylinders shown in FIG. 2A is a serial one, but the connection can equally well be a parallel one as shown in FIG. 2B.

Figure 2B:
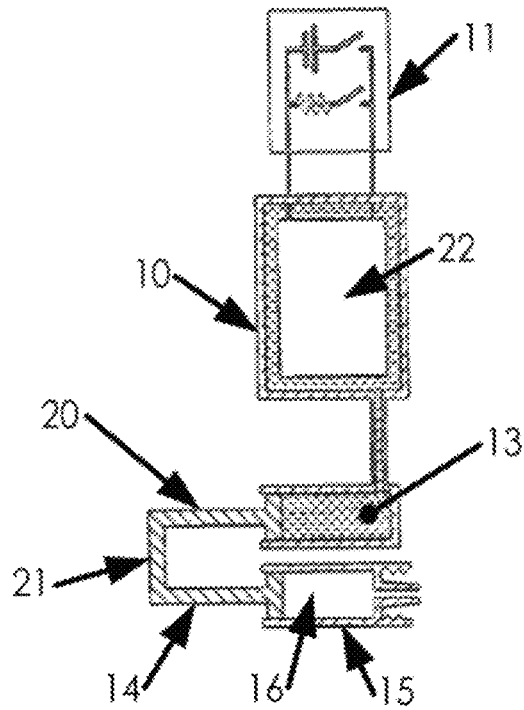
Figure 2C:
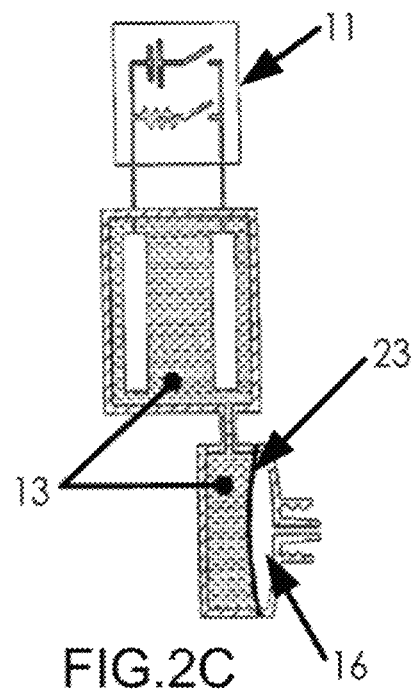
Figure 2D:
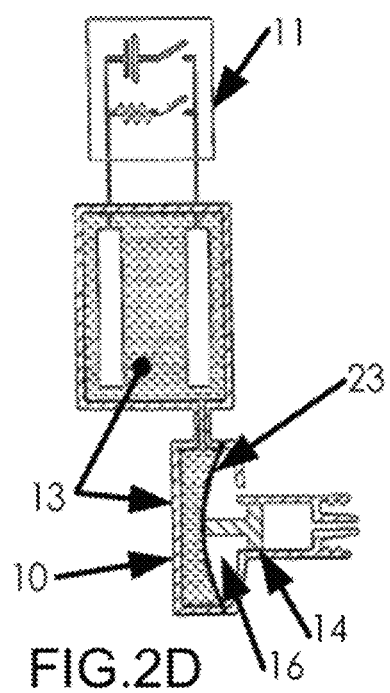

Referring now to FIG. 2B, a mechanical link 21 serves to couple the piston 14 of the drug chamber 15 with the piston 20 of a control cell 10. The control cell 10 comprises a sealed volume-changing or shape changing element 22 and a hydraulic fluid 13 external to the sealed unit. The sealed volume-changing or shape-changing element 22 can be: (a) an electrochemical cell as described above; (b) a solid-state device such as an electroactive polymer, with two contacts attaching it to the electric circuit 11, or (c) a solid-state battery such as a lithium-ion battery. In this preferred embodiment, the volume contraction of the sealed unit 22 is conveyed to the rest of the mechanism by the hydraulic fluid 13 as opposed to being conveyed by the electrolyte participating in the chemical reaction within an electrochemical cell. Advantageously, when employing an electrochemical cell within the sealed unit 22, this arrangement isolates the electrolyte from the piston arrangement, simplifying the materials choice while also ensuring better isolation of chemicals in case of leakage. It will be clear to one skilled in the art that the coupling between the control cell 10 and the drug chamber 15 may be achieved via any coupling means including but not limited to mechanical bar mechanisms, mechanical trains, pulleys, and the like, resulting in either proportional motion or a more complex exponential correlation. For example, FIG. 2C shows a non piston-based mechanical arrangement, where flexible wall 23 constitutes the displaceable wall between the control cell 10 and the drug chamber 15. The flexible wall 23 may either exert pressure on the drug 16 directly or via the use of a piston 14 as shown in FIG. 2D.

In a preferred embodiment, this system implements one of the battery or fuel cell systems such as those described above, including but not limited to nickel-cadmium (NiCad), Formate/MnO2 fuel cell and dry cells. However, purely to demonstrate the volume change concept, the volume change associated with the well-known lead acid battery system is provided in Table 1 below which provides the molecular weights, densities and volumes of the reactants (on the left-hand side) and the products of this reaction on the right-hand side:

TABLE 1

|  | Pb | $PbO_2$ | $2H_2SO_4$ | $2PbSO_4$ | $2H_2O$ |
|---|---|---|---|---|---|
| Mol. Wt. (gm) | 207 | 239 | 196 | 606 | 36 |
| Density | 11.3 | 9.4 | 1.8 | 6.2 | 1 |
| Volumes (cc) | 18.3 | 25.4 | 108.8 | 97.7 | 36 |
| Total volume | | | 153.5 | | 133.7 |

As will be seen from Table 1, the total volume of the reactants and products, given one mole of reagents, is reduced on discharge from 153.5 cc to 133.7 cc, which is a 19.8/153.5 contraction, or a 13% decrease. The above reaction operates at 2V and according to Faradays Law provides 2 Faradays (53.6 Ahr). A volume or shape change of 0.2 cc for example, would thus require a cell of capacity 0.2/19.8× 53.6 Ah=0.54 Ah.

Embodiments of the present invention include the use of any kind of non-gas evolving shape-changing or volume-changing means where the means is connected via contacts to an electrical or electronic circuit; such that the passing of current across said contacts causes a volume or shape change. At its simplest, this circuit is just a resistor via which a battery-type volume-changing or shape-changing means is discharged. Alternatively, the circuit is a battery and the volume-changing or shape changing means is a passive electrochemical cell or electroactive polymer. Where an electrochemical cell is employed as the volume-changing or shape-changing means, the volume or shape change is typically the change of the combined volume of liquids, solids, pastes, and gels within the cell. In the case of a fuel cell, the internal fuel is consumed and thus the volume decreases. Note that a fuel cell will further comprise additional elements including a fuel compartment and an inert catalytic electrode to provide the fuel oxidation reaction. In its simplest embodiment a fuel anode coupled with an oxide cathode such as manganese dioxide could be used; although air could be used as the cathode instead. A further special case is the use of batteries which react with air such as zinc-air batteries. In this case, in embodiments of the present invention the air is stored internally to the battery casing, such that as this air is consumed, the battery volume contracts.

Referring now to FIGS. 3A and 3B, further preferred embodiments of the drug-delivery device of the present invention are shown. In such preferred embodiments, a reverse-brake configuration is employed, whereby the motion of the piston 14 due to the driving force of the spring 31 is restrained by the electrolytic fluid 13. FIG. 3A shows the reverse-brake configuration where the two cylinders (cell and drug) are positioned in series such that the movement of the piston 14 is driven by the spring 31; and FIG. 3B shows the configuration where the cylinders are positioned in parallel such that the mechanical link 21 couples the movement of the pistons (20 and 14) into them. The advantages of this approach and further details of its implementation are described in International Publication No. WO 2004/067066, which is incorporated herein by reference. According to some embodiments, the connection between the cylinders (i.e. the drug chamber and the electrochemical cell) can be any kind of mechanical hydraulic, magnetic or other coupling means known in the art; and the coupling action may result in either a proportional or an exponential correlation between a multiplicity of such drug chambers 16 and a multiplicity of such cells 10. Note that in certain systems according to this embodiment the driving force will be the combination of the force exerted by the spring and the contraction/expansion of the cell.

Figure 4:
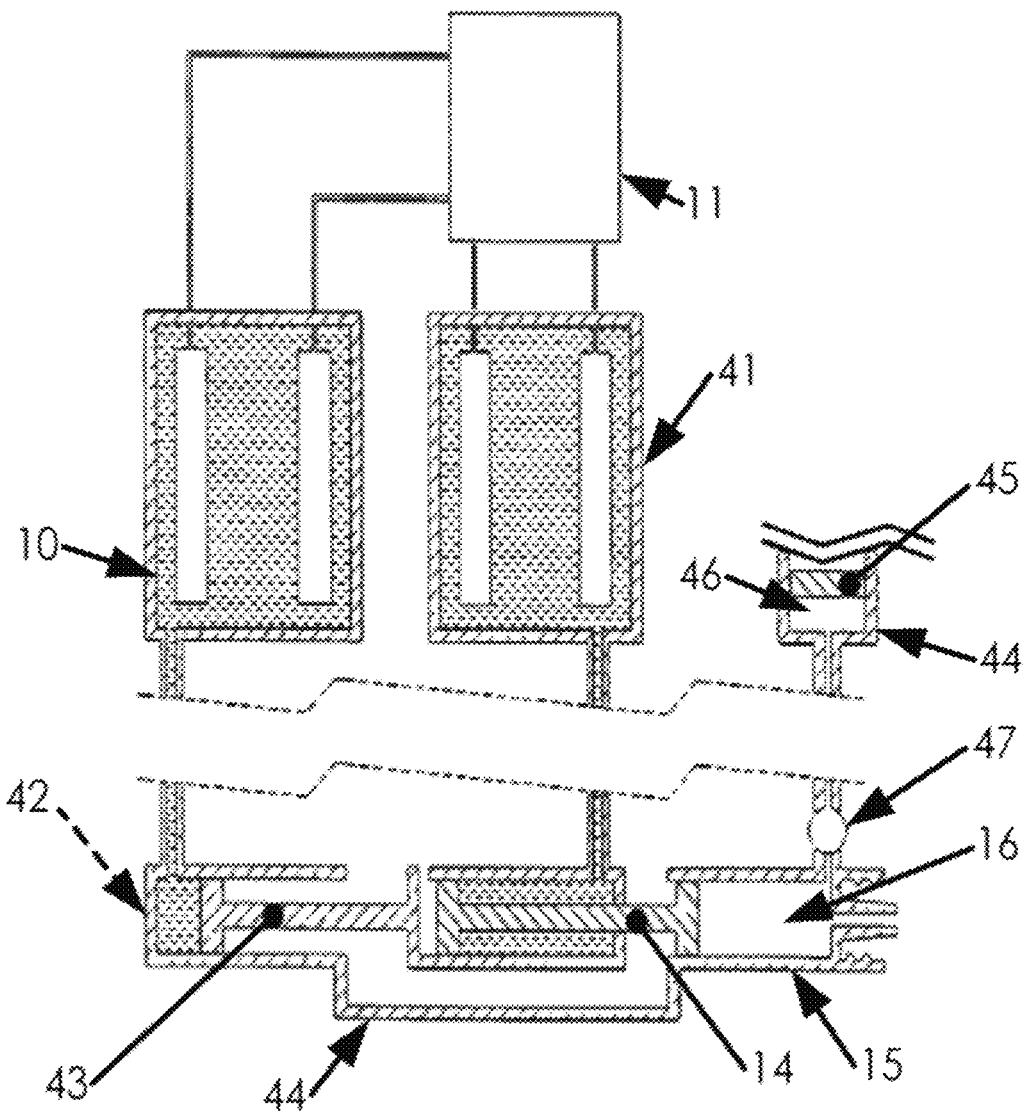

Whereas the embodiments above describe relatively simple configurations of the drug-delivery device of embodiments of the present invention, the general principles involved in the invention enable the implementation of a large number of further embodiments; the further embodiments addressing further issues in such devices, such as refilling, drug dilution and implantable versions. For example, referring now to FIG. 4, an additional electrochemical cell 41 is employed in order to enable two-way motion of the piston 14 without an external power source; the motion proceeding as follows: (a) As a first cell 10 is depleted, the piston 14 is driven into the drug chamber 15 as per the previous embodiments. (b) As the volume within the second cell 41 contracts, the piston assembly 43 is withdrawn into its housing 42; the assembly 43 also constituting the housing of the cylinder surrounding piston 14. As the housing 42 is connected by rigid member 44 to the drug cylinder 15, the withdrawal of the piston assembly 43 into said housing 42 causes the piston 14 to be (slowly) extracted from the drug chamber 15. Thus, purely by controlling the discharging of two electrochemical cells (10 and 41), motion of the piston 14 into and out of the drug chamber is achieved. This two-way motion is especially advantageous where refilling of the drug chamber is required. An additional electrochemical cell may be employed that exhibits volume displacing properties to be used for fast expansion during priming of the pump.

A major objective when designing an implantable drug-delivery device is to enable it to work over an extended period that could extend to several years. One solution to this issue is to provide a filling port accessible from the patient's skin. However, such filling ports are notoriously susceptible to contamination, making this approach a very problematic route. Embodiments of the present invention enable an improved approach whereby a second drug chamber 44 contains a highly concentrated form of the drug to be delivered. After each completed cycle of drug delivery (i.e. when the piston 14 has advanced to the right-hand end of the drug chamber 15), the two-way motion of the mechanism is exploited to gradually withdraw this piston 14 to the left. As said piston 14 is withdrawn, a small amount of the drug concentrate 46 from the second or reservoir chamber 44 is introduced to the drug chamber 15 via non-return valve 47 due to the pressure of displaceable wall 45 on said drug concentrate 46. Further, as the piston 14 continues to withdraw, body fluids will enter the drug chamber 15 through the chamber's outlet port; the fluids serving to dissolve and/or otherwise dilute said drug concentrate 46. On reversing the direction of the piston 14 yet again when the drug chamber has refilled, the now diluted drug will start to be delivered as before; i.e. the next cycle can begin. According to some embodiments, the concentrated drug can be in either liquid or solid form, and the mechanism as described above can provide drug delivery over an extended period without requiring external refilling. Likewise, the ability to use the drug-delivery device of the present invention to perform intake of body fluids enables the device to further incorporate various body fluid sampling and/or analysis elements.

Figure 5:
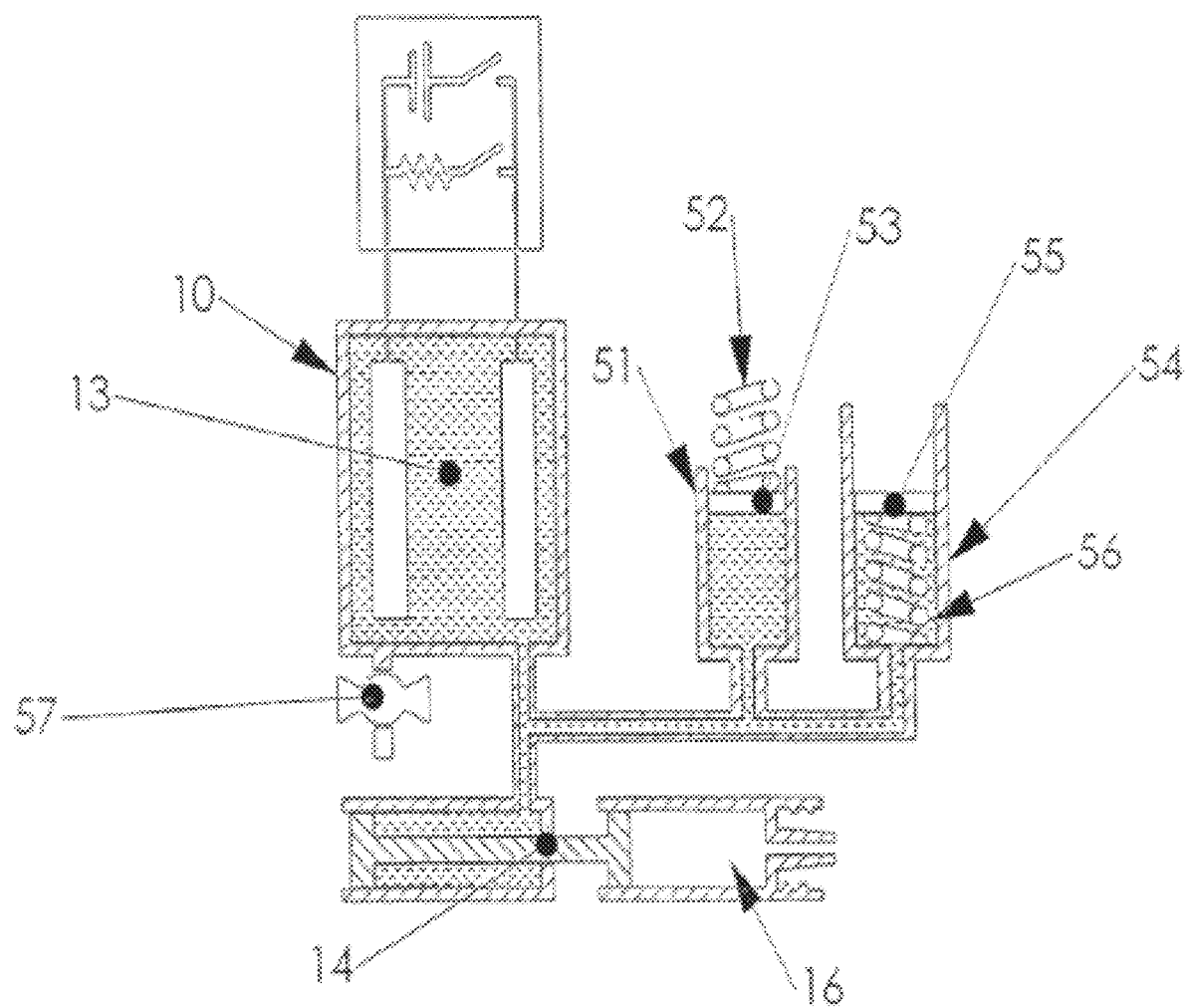
FIG. 5 provides a block diagrams showing the addition of further hydraulic elements, according to embodiments of the present invention.

All the above embodiments relate to the case where the volume enclosing the entire hydraulic system remains constant except for the displaceable wall or piston. Accordingly, in this case, the volume-changing or shape-changing means is the only changing factor and thus its change is directly expressed in the movement of the piston. Referring now to FIG. 5, the addition of further hydraulic elements to the system is presented, whereby the volume enclosing this hydraulic system can be increased or decreased. These hydraulic elements include: (1) an injector 51 whereby, on release of the spring 52, the inner volume of the injector 51 is subtracted from the total volume of this hydraulic system, thereby causing the piston 14 to advance and expel the drug 16; (2) an extractor 54 where, on release of its internal spring 56, the extractor causes the piston 14 to retract, thereby adding to the total volume of this hydraulic system; and (3) a filling and/or drainage port that can be used in conjunction with the reversal of either of the above steps. According to some embodiments, displacement caused by such springs could equally well be performed by numerous alternative actuation means, including but not limited to electric motors such as linear motors, solenoids, magnetic coupling or a further electro-chemical actuator.

Figure 6A:
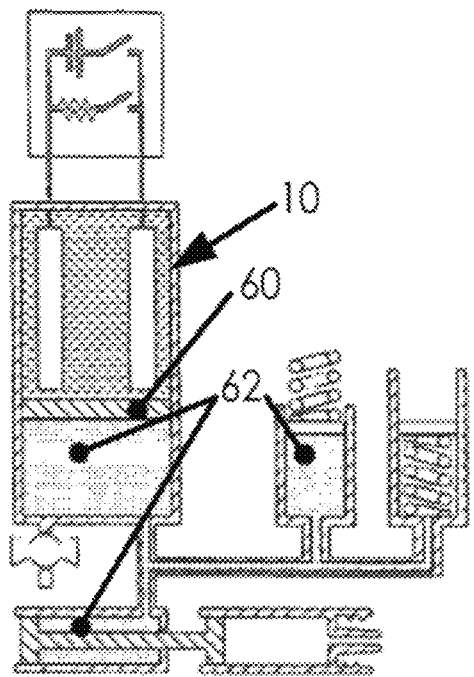
FIGS. 6A and 6B provide block diagrams showing the addition of further hydraulic elements, according to embodiments of the present invention.

According to some embodiments, it is not necessary to use the electrolyte as the hydraulic fluid throughout the entire system. Instead, and referring now to FIG. 6A, a displaceable wall in the form of a moveable partition 60 is located within the electrochemical cell 10 such that the volume change or shape change produced by said cell is conveyed via a hydraulic fluid 62 to the rest of the system. This arrangement is advantageous as per the description of FIG. 2B above. The figure shows a 1:1 volume or shape displacement ratio but according to some embodiments the movable partition and cylinder can have different diameters on each end, resulting in a different fluid displacement ratio.

Figure 6B:
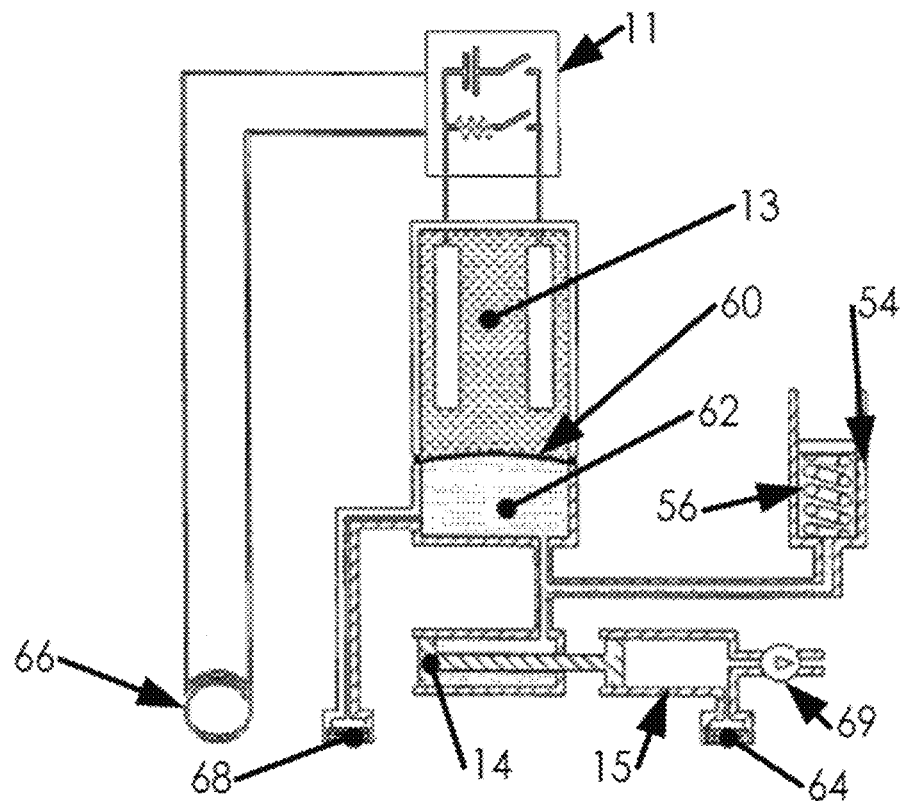

Referring now to FIG. 6B, a preferred embodiment of the drug-delivery device of the present invention is shown, optimized for implantable use, with an external filling port. This embodiment illustrates a number of potential ways in which the piston 14 can be withdrawn so that the drug chamber 15 can be refilled via filling port 64, typically by means of a septum. One way in which the piston 14 can be withdrawn is by charging the electrochemical cell 10, either by direct external electrical connection (not shown) or, preferably, by a magnetic induction coil 66. A second way to accomplish this objective is to use an injector 54 as per FIG. 5 above; and the third is the introduction of hydraulic fluid 62 via a hydraulic fluid filling port 68, also equipped with a septum. This embodiment also illustrates the use of a flexible membrane as the displaceable wall 60 within the electrochemical cell 10, and the use of a non-return valve 69 at the outlet of the drug chamber 15, to prevent ingress of body fluids.

Referring now to FIGS. 7A, 7B, and 7C, a preferred embodiment of a miniature implementation of the drug-delivery device of the present invention is shown. FIG. 7A shows an exploded isometric view of said device, comprising a printed circuit board (PCB) 70, a rigid lower cover 72 of the control cell which also serves as part of the outer housing of the device, the flexible upper wall 74 of the drug chamber, hydraulic jacks 75 which are in fluid connection with the control cell below and attached to a rigid plate 77 above, and a septum 76. The septum may have an asymmetrical shape, ribbed, have a small cavity at either or both ends, and any reasonable combination of these features. Referring now to FIG. 7B, the view from below of the PCB is provided, showing two electrodes 12 on its surface. The electric or electronic control circuit 11 may be implemented in the same PCB, terminating at the electrodes 12. In its simplest embodiment, the circuit 11 is simply a resistor that is placed across the ends of the electrodes 12 when an external rim to the device (not shown) is rotated to the "on" position. Referring now to FIG. 7C, a cross-sectional view of the device is shown where the functional role of all the above components is shown. Starting with the control cell 10, it is seen that this cell is formed between the rigid lower cover 72 of the device and the PCB 70 above, and contains electrodes 12 and an electrolyte 13 which serves as a hydraulic fluid. The liquid volume of said cell 10 is shown to extend through holes in the PCB 70 to the hydraulic jacks. As the liquid volume in said cell 10 is reduced, the jacks 75 retract toward the PCB 70, thereby exerting force on the rigid plate 77 to which they are attached. Note that the drug chamber 15 is formed between the PCB 70 and the flexible upper wall 74. As the rigid plate 70 is pulled towards the PCB 70 by the contraction of the hydraulic jacks 75, the drug 16 enclosed within the drug chamber 15 is gradually expelled through the cannula 17. In this embodiment, the cannula 17 is typically a Teflon™ one, which is inserted into the body using a needle 79 which is inserted via the septum 76. According to some embodiments, additional elements incorporated in the insertion means may include a safety feature to protect against accidental contact or injury.

Figure 7D:
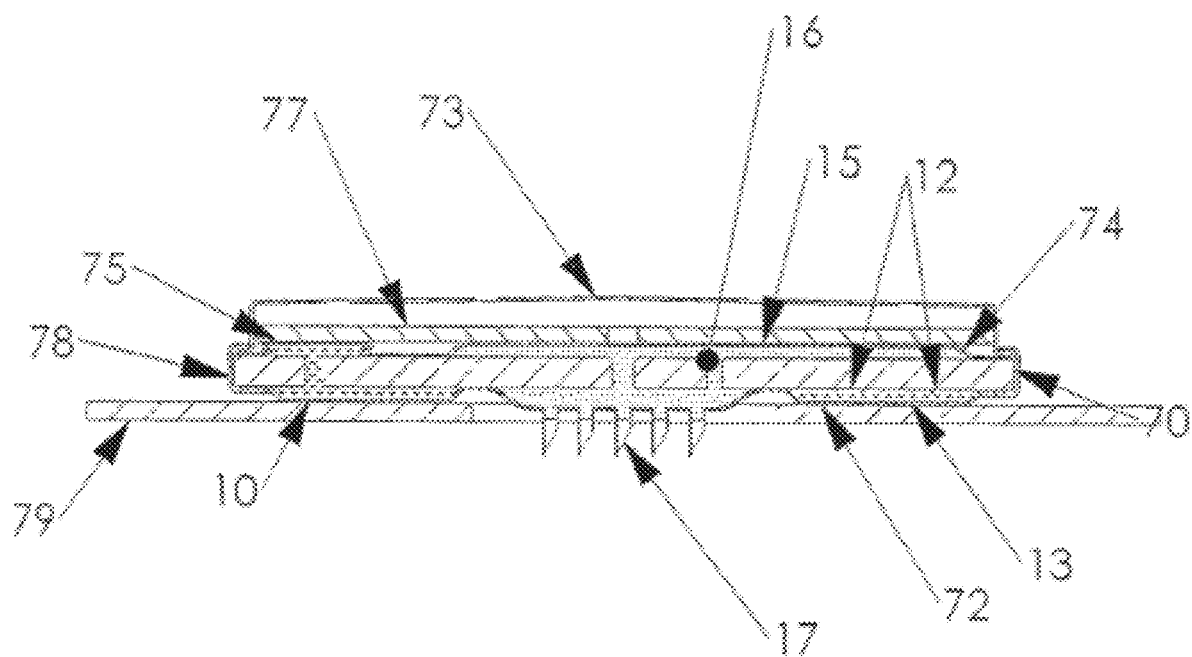

Referring now to FIG. 7D, a further preferred embodiment of the drug-delivery device of the present invention is shown. In this embodiment, the needle 79 and septum 76 are obviated as the drug administration means in this case is a mini-cannula or micro-cannula array 17 which does not require external insertion means. This figure shows the mechanism at an advanced dispensing stage so that the hydraulic jacks 75 and the flexible wall 74 serving as the upper wall of the drug chamber 15 are partly empty or collapsed. It also shows the entire assembly further comprising an adhesive patch 79 for attaching the device to the body and a stainless steel enclosure 78 surrounding at the least top and sides of the device, where said enclosure 78 can also serve as a rotating component used as a switch to activate the device and/or regulate the dosing rate. The rotating action can also provide a lock/lock release to the dispensing mechanism to avoid inadvertent activation. Note that in both this embodiment and the previous one, a hole is required in the rigid plate 77 so that air trapped between it and the flexible wall 74 is evacuated as the plate 77 descends. Device embodiments of the present invention may be further provided with an air compensation means implemented in its external enclosure so that the mechanism may freely contract as it operates. The means may include a flexible wall, a gas-permeable (and preferably hydrophobic) membrane, or simply an air hole.

Note that both of the above embodiments (as per FIGS. 7C and 7D) can be provided with either a single-use or a multi-use insertion device; whereby the drug-delivery device will be attached to the skin and have the cannula(s) inserted into the body by a single and simple non-disturbing action. In a further preferred arrangement, said insertion action also automatically operates the device. Additionally, the materials used for the cannulas or mini/micro-cannulas and/or the adhesive patch may include an eluting element to gradually release an anesthetic or anti-inflammatory drug to the skin. The use of eluting materials for fabricating stents is well known in the art, and this approach can be used for example on the rigid cannulas to minimize the pain involved. Alternative means of attaching the drug-delivery device of the present invention include straps and clasps.

Referring now to FIGS. 8A to 8E, various views of a preferred embodiment of the drug-delivery device of the present invention based on the "parallel" design of FIG. 3B above are provided. Referring now to FIG. 8A, an isometric exploded view of this device embodiment of the present invention is provided, showing a piston assembly comprising control cell pistons 20 and a drug cell piston 14, joined by a mechanical link 21; and a housing 81 containing the cylinders for the pistons, the housing 81 providing the cylinders for the drug chamber piston 14 and the control cell piston 20. Note that in this embodiment two control cells 10 are provided in parallel for safety reasons, such that even if one of them should develop a leak, the brake effect discussed in relation to FIG. 3 above would continue to operate and a massive drug dose to the patient would be prevented. The electrode assemblies 83 each hold two electrode plates 12, with a fixed spacing. Referring now to FIGS. 8B and 8C; two planar views (from above and from the side respectively) of this embodiment are shown; the lines A-A and B-B provide the cut line for showing the cross sections shown in FIGS. 8D and 8E respectively. Referring now to FIG. 8D, a cross-sectional view of the assembled device is provided showing how the pistons enter their respective cylinders. In a preferred embodiment the area ratio of the two types of pistons enables the determination of the ratio effect required. For example, using a 10:1 ratio between the area of the drug chamber piston 14 and that of the cell piston would enable a relatively small change in the volume of the drug chamber (say 0.2 cc) to drive a drug-infusion of ten times that amount (2 cc). According to some embodiments, reversing the ratio can enable the opposite effect. Also clearly seen in this cross-sectional view is the way in which the electrochemical control cell 10 contains one contiguous volume, part of which is inside a cylinder and part (the majority) is external to said cylinder. The excess of electrolyte and electrodes size enables longer strokes as the shrinkage of the cell is limited. Referring now to FIG. 8E, the placing of the electrodes within this latter, external volume, is seen. This structure enables the electrodes 12 to contact the electrolyte as a whole, while only a subsection of the electrolyte is gradually depleted from the narrow cylinder. In combination with the piston ration described above, this arrangement enables a relatively small discharge to power a significant drug infusion. In this preferred embodiment, the pistons are free to move in accordance with the expansion/contraction of the volume in the cell 10. Various kinds of O-rings or other means known in the art may be used to seal the interface between the pistons and their respective cylinders such that the system is maintained sealed.

Regarding the electrical or electronic control circuit of the drug-delivery device of the present invention, it will be apparent to those skilled in the art that a wide range of electronic control systems (not shown) may be incorporated within (or interfaced to) said device. The range includes: (a) microprocessor-controlled variable-resistance or load elements for controlled discharge of the cell; (b) removable control units that enable a semi-disposable device to be constructed whereby all or part of the control circuitry may be moved from disposable section to disposable section; (c) systems comprising a remote-control element; (d) systems that interface to a flow-control feedback element monitoring the actual drug delivery rate, either directly or indirectly; (e) an interface control unit that receives signals related to medical parameters such as blood-glucose levels, other blood-analyte levels and body temperature; and (f) any combination of the above. Advantageously, where the control cell is also a battery cell, the electronics circuit and/or electronic control systems may be at least partially powered by the very depletion of power that drives the drug-delivery device, thereby in many cases obviating the need to provide a battery to power the electronics of such a device. Additionally, in the case of an implanted device, the design may further employ embedded electronics sealed by resin casting or other sealing means known in the art, and various communication means including but not limited to magnetic coupling transmission, RF or IR transmission.

In some cases, more sophisticated embodiments are possible which combine a multiplicity of drug cells and a multiplicity of electrochemical cells, in every possible arrangement or interaction with each other, and combining every possible coupling means including hydraulic, mechanic, magnetic, and the like.

Preferred chemical systems for an electrochemical cell within the drug-delivery device of the present invention are those which are non-gassing or in which there is minimal parasitic gas production. Nevertheless, in the case that the selected chemical reaction does generate gas, said gas may either be vented via a gas-permeable membrane or recombined via a catalytic plug such as those made by Hoppecke Battery Company, Germany. As all cell walls other than the displaceable one must remain fixed and rigid in order to maintain the accuracy of the slow-infusion device, it is important that such membrane be provided with an appropriate support structure so as not to detract from the rigid structure of the cell. These gas eliminating means are arranged in a fashion that efficiently operates in every operational orientation of the device. Suitable gas-permeable membranes include Fluoropore™ membrane from Millipore Inc. (Billerica, Mass., USA) and Emflon™ from Pall Inc. (East Hills, N.Y., USA).

Figure 9A:
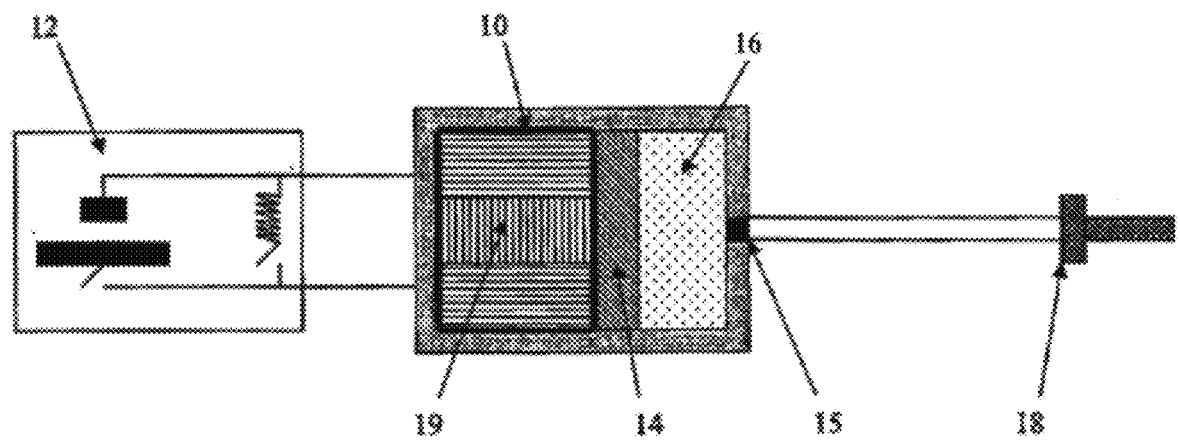
FIGS. 9A and 9B provide block diagrams of an overall drug-delivery device, showing its main components, according to embodiments of the present invention.
Figure 9B:
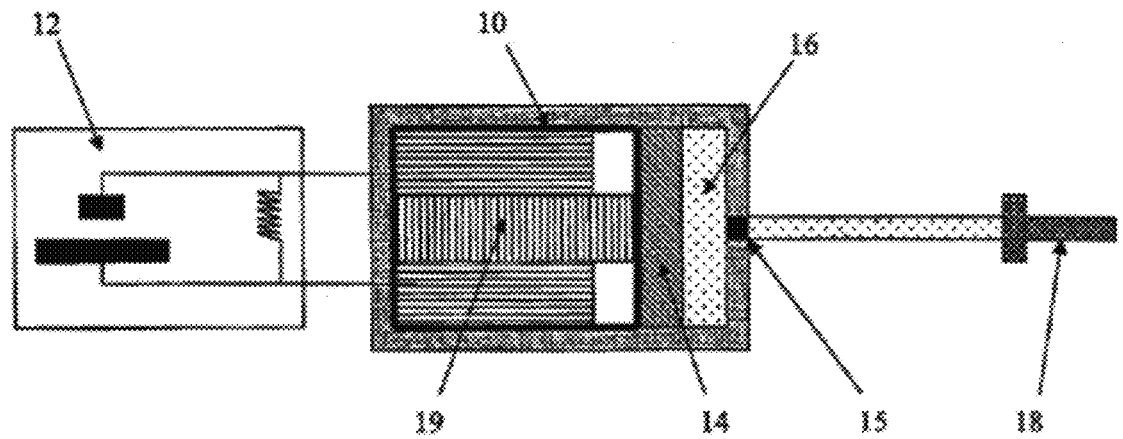

Referring to FIG. 9A, a simplified block diagram of the drug-delivery device of the present invention is shown so as to illustrate the main components involved. In this illustrative embodiment, a battery cell 10 is shown adjacent to a drug chamber 16 with a displaceable wall 14 between them, such that expansion of the volume-changing or shape-changing component 19 of the battery 10 causes the displaceable wall 14 to decrease the volume of the drug chamber 16. The battery 10 is activated and controlled by the control circuit 12; the activation of the battery 10 causing its volume-changing or shape-changing component 19 to expand in this example. The expansion causes the drug chamber 16 to contract such that the drug is expelled through the drug administration means 18. In a preferred embodiment, the expulsion takes place via a valve 15 leading to drug administration means 18. Referring now to FIG. 9B, the situation after the battery 10 has been activated is shown, illustrating the significant change in volume or shape of its volume-changing or shape-changing component 19. Note that, depending on the battery chemistry, the electric circuit will either discharge the battery 10 in order to cause the volume or shape change, or charge the battery in order to achieve this change. For this reason both a battery and a resistor are shown within the block diagram of said circuit 12 for a schematic representation of its functionality. If the depletion method is used, advantageously this obviates the need for having a further battery cell to power drug-delivery device, according to some embodiments of the present invention, as the device is thereby self-powered to some extent, further reducing costs. Note also that the volume-changing or shape-changing component 19 of the battery cell 10 does not have to be an expanding component as shown but could, by a slightly different mechanical arrangement be a contracting component.

Figure 10A:
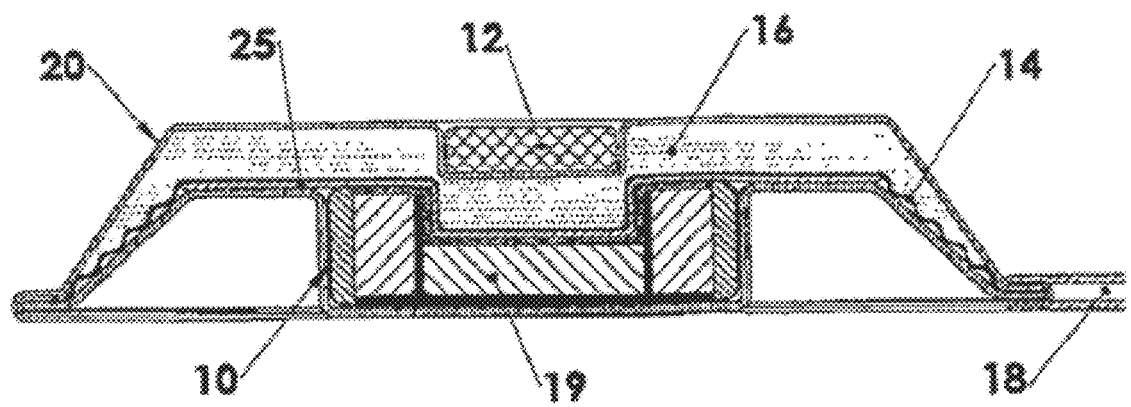
FIGS. 10A to 10C provide cross-sectional and isometric views of preferred embodiments of a drug-delivery device with a displaceable wall between the battery cell and the drug chamber.
Figure 10B:
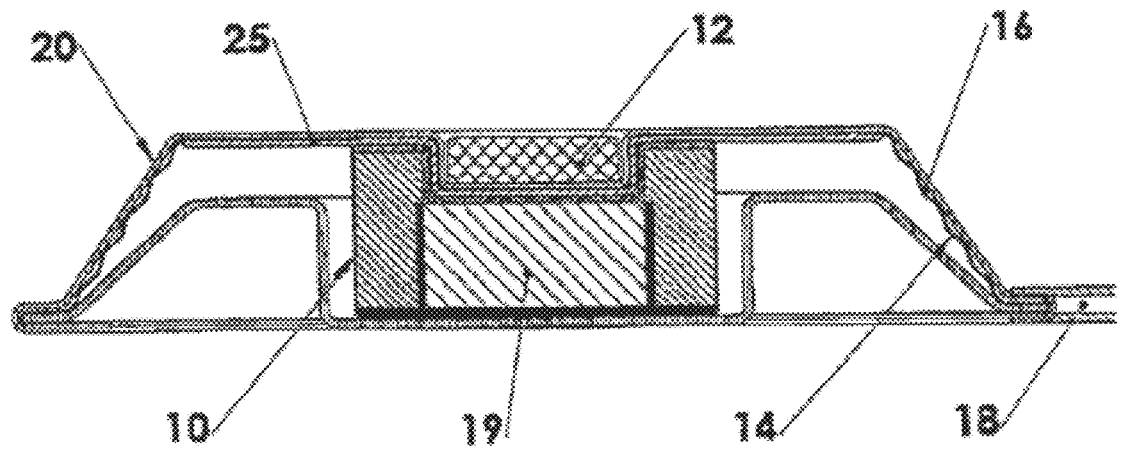

Referring now to FIGS. 10A and 10B, a cross-sectional view of a preferred embodiment of the drug-delivery device of the present invention is provided. FIG. 10A shows the configuration prior to activating the battery, while FIG. 10B shows the configuration of this device at the end of the device's operation. This embodiment comprises a housing 20 which contains the battery 10 and a drug chamber 16. In this embodiment, the expansion of the battery 10 moves a coupling means 25 in a shape of a plate which in turn displaces the displaceable wall 14 and reduces the volume of the drug chamber 16, causing the drug to be expelled via the administration means 18. In the preferred embodiment shown, the plate 25 is covered by a displaceable wall 14 of the drug chamber 16, the displaceable wall 14 incorporating a bellows-shaped circumference. In this preferred embodiment, the use of the displaceable wall 14 in this manner enables the optimal use of the drug chamber 16 shape in that the chamber 16 can be almost completely depleted by the displacement of the plate 25. Additionally, the bellows section of this displaceable wall 14 provides a counter-force to the force generated by the cell 10, ensuring that the displacement produced operates in a controlled fashion and is less susceptible to motion artifacts. According to some embodiments, such a counter-pressure effect can alternatively be performed by the use of any other counter pressure means including but not limited to springs, or other compressible elements. The volume or shape change under the displaceable wall 14 will be compensated either by having an opening (not shown) to the ambient air through the bottom side of the housing 20 or by using any other volume compensation means known in the art. An electronic control unit 12, which controls the discharge of the battery 10 is further incorporated in the drug-delivery device. The control unit 12 may be interfaced with a pressure sensor (not shown) located either within the drug chamber 16, on the walls of the drug chamber 16, or along the liquid path to the administration means 18, in order to serve as the occlusion detector and send a signal back to the control unit 12 to stop the activation of the battery 10. According to some embodiments, a suitable wiring arrangement (not shown) whereby both polarities of the cell 10 are connected to contacts attached to the control unit 12 is provided. Suitable materials for the housing 20 include plastics including but not limited to polyethylene (PE) and polypropylene (PP), or metal such as stainless steel; and suitable materials for the displaceable wall 14 include stainless steel, aluminum, rigid plastics or multilayer films.

Advantageously, this embodiment uses a small, lightweight battery 10 which has a small diameter relative to the diameter of the housing 20; such that the resulting device is light relative to the volume of drug it can deliver. For example the diameter of the battery 10 can be 10-30 mm, while the diameter of the drug chamber 16 is 20-60 mm correspondingly. Thus an amplification effect is achieved whereby a relatively narrow piston presses upon a drug chamber of broader proportions. Note that this does require relatively high force to be generated by the battery cell 10, but the cells described in the preferred embodiment below successfully generate this force.

Figure 10C:
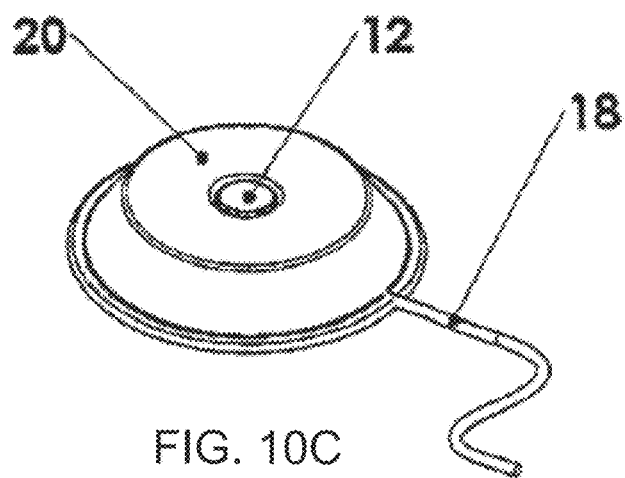

Referring now to FIG. 10C, an isometric view of a drug-delivery device embodiment of the present invention is provided, showing the housing 20, an electronic control unit 12 inserted into a recess in said housing and a delivery means 18 shown here as a thin tube. The housing 20 further comprises an air-evacuation channel (not shown) for the evacuation of air from said recess as said control unit 12 is inserted. The control unit 12 may be a disposable, semi-disposable or permanent one. Where it is either semi-disposable or permanent, it may interlock with a location on the drug-delivery device (for example as shown in the present embodiment) so as to enable easy insertion and removal. Advantageously, making this control unit 12 re-usable reduces the cost of using drug-delivery devices embodiments of the present invention, as then the cost of one control unit 12 may be spread over the use of many disposable devices. In a preferred embodiment, said battery cell 10 is simply discharged (in a controlled manner) by said control unit 12, making such a device embodiment of the present invention in effect self-powered. Some examples of different delivery means suitable for use with this device are provided within the context of FIGS. 12A to 12D below. The design can be either a circular one as shown, or a square design can be used. The unexploited space in this embodiment can, advantageously, be used for the electrical components such as sensors, buttons and/or a buzzer (all not shown). According to some embodiments, all the elements of the drug-delivery device and its internal wiring are protected against environmental influences such as humidity.

In some embodiments, the drug does not have to be in direct contract with the displaceable wall 14 and the inner surface of the housing 20, but rather can be maintained within a flexible pouch. Suitable materials for fabricating such a drug pouch include but are not limited cyclic olefin polymer (COP) and cyclic olefin co-polymer (COC), to high-density polyethylene (HDPE) and polypropylene (PP) or any type of multi-layer film including such materials. Polyethylene terephthalate (PET) and polycarbonate (PC) may also be considered. From a regulatory perspective, this embodiment is advantageous as it enables the drug-filling to be performed in a separately controlled and regulated fabrication environment, while the integration of the pouch into the complete drug-delivery device can potentially be performed in a less controlled environment.

Figure 11A:
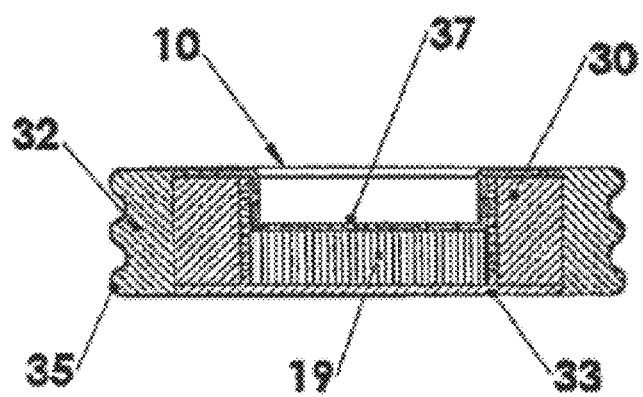
FIGS. 11A to 11D provide cross-sectional and isometric views of preferred embodiments of a battery cell for use within the present invention.
Figure 11B:
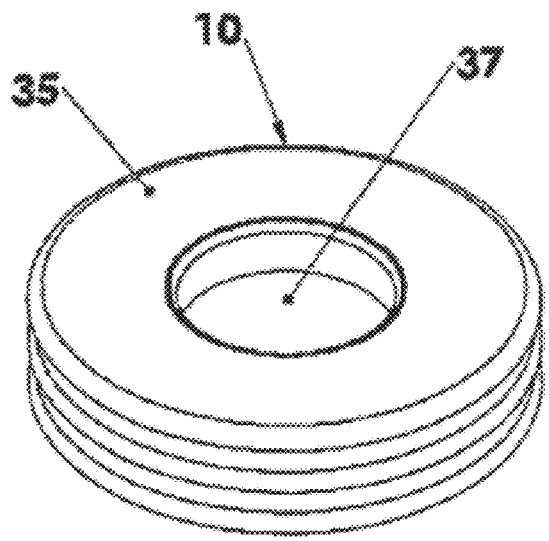

Referring now to FIGS. 11A to 11D, a preferred embodiment of the battery cell 10 which drives the drug-delivery device is shown. In a preferred embodiment, the lithium-tin battery chemistry is employed. FIG. 11A provides a cross-sectional view of said cell showing its internal structure, while FIG. 11B provides a isometric view showing the concertina-like structure formed; both showing the initial state of the cell 10 before activation. As shown in FIG. 11A, said cell 10 comprises a flexible metal sheet housing 35 formed according to a concertina-shaped design; said housing 35 containing a lithium anode 30 and a tin cathode 19 which, in this embodiment, is the expanding element. The cell 10 further comprises a rigid cylindrical metallic mesh 33 which surrounds the tin cathode 19; there being also a separator (not shown) between the lithium anode 30 and said mesh 33. Thus the arrangement of the battery components is a concentric cylinder one, where all the remaining volume within the cell 10 is taken up by the electrolyte 32. In this preferred embodiment, the electrolyte 32 used for the lithium-tin system is a solvent of a mixture of ethylene carbonate and ethyl methyl carbonate with dissolved lithium hexafluorophosphate as the ion-providing (ionizing) salt. As the cell 10 is depleted, the lithium ions penetrate the tin cathode 19 causing it to expand. In the present embodiment, said expansion is constrained to take place primarily in the vertical direction due to the rigidity of the mesh 33 which prevents expansion to the sides. Said expansion therefore takes place against the rigid battery cap 37. In this embodiment the cap 37 serves as one pole of the battery and the housing 35 serves as the second pole. The sealing between the cap 37 and the housing 35 is electrically insulated. The wiring from the control unit will be connected to these battery poles. The housing 35 can be made from materials other than metal such as multilayer films as described in U.S. Pat. Nos. 5,134,046, and 6,296,967 which are non-conductive, and the wiring arrangement can be as known in the art, for example as per U.S. Pat. No. 6,296,967.

Figure 11C:
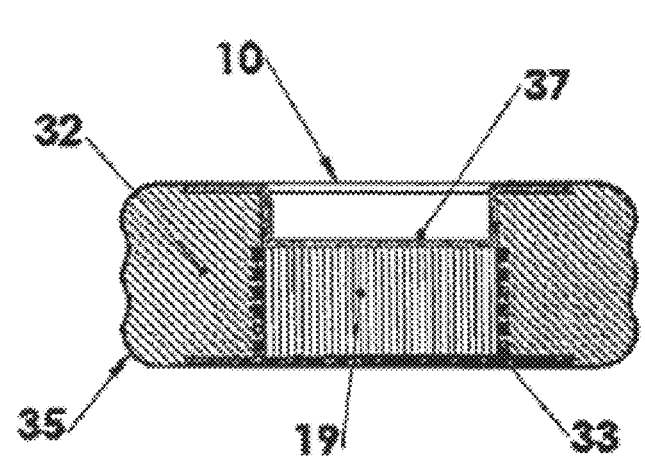
Figure 11D:
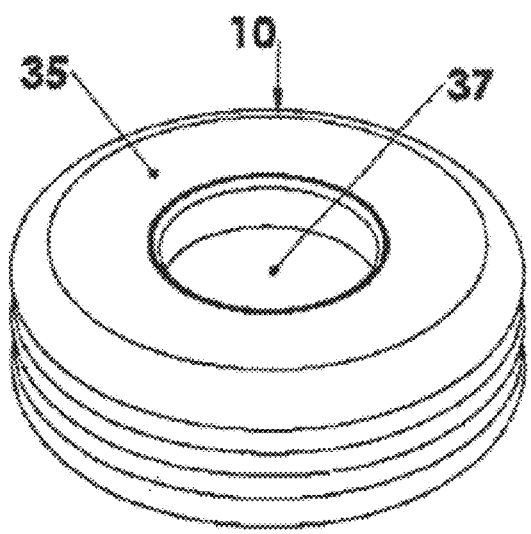

Referring now to FIGS. 11C and 11D, the state of the battery cell 10 as it is fully depleted is shown, in cross-sectional and isometric views respectively. Full depletion means that all the lithium ions have migrated into the tin cathode 19, leaving only electrolyte 32 behind. The resulting expansion of the tin cathode 19 has raised the position of the battery cap 37, causing an overall change in the shape of the cell. The change is enabled by the flexible nature of the cell's housing 35. In the preferred embodiment shown, the flexible concertina shape shown is readily adaptable to the new configuration of the battery cell 10, as it adjusts to being lengthened by reducing the extent of the folds in the side walls and at the same time moving inwards in order to adapting to the overall volume or shape change in the cell. In this manner, the cell 10 becomes taller but narrower to reflect the expansion of its volume-changing or shape-changing component.

Note that in this preferred embodiment, the tin cathode 19 needs to be highly porous while also preserving mechanical strength. In a preferred embodiment it is prepared by making a 2:1 mixture (by volume) of Sn powder and a powder of table salt, NaCl. This mixture was pressurized in a stainless steel mold under 5 tons of pressure to form the appropriately sized pellet. This pellet was then boiled several times in distilled water, with fresh portions of distilled water being used each time, and then, finally, sonicated in distilled water for 5 minutes. After drying and weighing the pellet, full dissolution of the NaCl was verified. In this way, highly dispersed and highly porous, yet mechanically stable Sn electrodes were prepared. The constraining of the Sn pellet as it expands was solved by designing a stainless steel mesh cylinder as a holder for this pellet. The porosity enables the lithium ions to penetrate the tin (via the electrolyte), while the mesh controls the direction of said expansion. Note also that in this embodiment, as the Li is consumed, it is important to concentrate the remaining Li close to this mesh, and thus a copper (Cu) net cylinder (not shown) surrounds the lithium for this purpose.

As will be obvious to one skilled in the art, a number of different embodiments of the battery cell 10 could be applied in the design of the cell. For example, the tin cathode 19 need not be constrained to only expand upwards, but could alternatively be constrained to expand downwards, or be allowed to expand in both directions simultaneously. Note that in the preferred embodiment shown, the lithium anode 30 extends higher than the tin cathode 19 so as to maximize the adjacent surface between the two, in order to enhance the ion transport. However, in order to produce a lower profile cell, an embodiment in which the initial height of both electrodes is close to identical may be used. In this embodiment, the ion transport is less efficient as the tin cathode 19 expands and the protruding part of it is no longer adjacent to the lithium anode 30, but this lack of chemical efficiency is a trade-off that may be worth making in order to enable the drug-delivery device to be miniaturized more effectively. In a further preferred embodiment, the arrangement of cathode and anode may be one employing parallel layers, one above the other; in or similar to the manner of a button cell. In a further preferred embodiment, a multiplicity of anodes and cathodes may be used to produce the desired displacement.

In a further embodiment the construction of the battery cell is on a Printed Circuit Board (PCB): the electrodes will be selectively "printed" on the circuit board in contact with conductive channels. The area of the electrodes will be confined under a flexible first cover sealed to the PCB and filled with electrolyte, said first cover being the displaceable wall of the battery. In a preferred embodiment a cover is placed around said first cover and sealed against the PCB, forming the drug chamber. According to some embodiments, any fashion of coupling means can be introduced between the displaceable wall of the battery and the displaceable wall of the drug chamber. The control circuit can be placed on the same PCB helping to further miniaturize the assembly and increase reliability. This embodiment is advantageous for small drug chamber applications where compactization is crucial such as implantable controlled drug release devices.

Figure 12A:
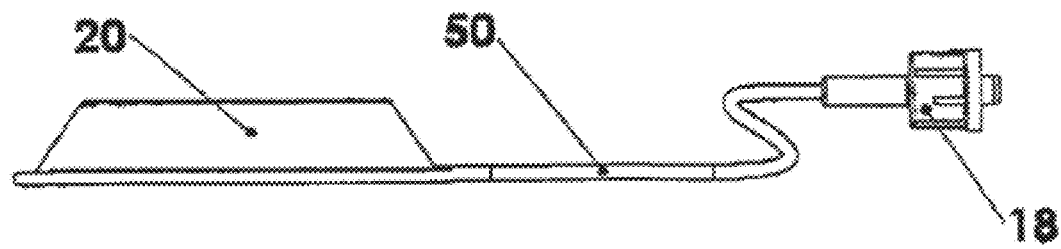
FIGS. 12A to 12D provide cross-sectional and isometric views showing the integration of a number of different administration means into the drug-delivery device, according to embodiments of the present invention.
Figure 12B:
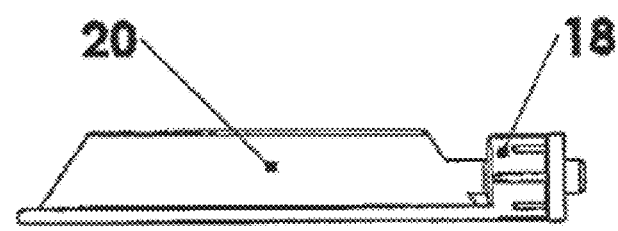
Figure 12C:
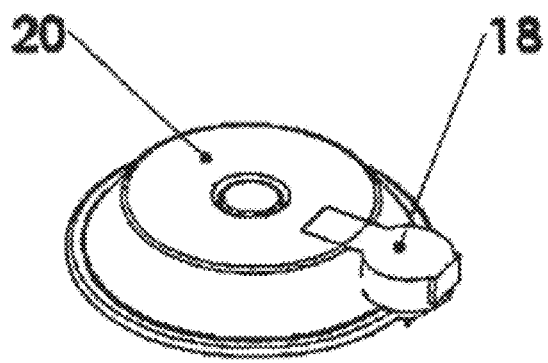

Referring now to FIGS. 12A to 12D, a number of alternative types of administration means 18 are shown. The administration means 18 can take numerous forms depending on the type of application for which the drug-delivery device of the present invention is being used. As will be clear to one skilled in the art, the administration means 18 can be any means whereby the drug or other substance delivered by the device enters the patient's body, including but not limited to an exit port in an implantable version of the device, and a cannula, cannula array or transdermal patch for an external device. In its simplest form the administration means is simply a conduit extending from the device. Referring now to FIG. 12A, the conduit 50 leads to a Luer lock, which is a standard connector to an infusion set. Alternatively, and as shown in FIG. 12B, the Luer lock is incorporated into the housing 20 of the device. In the further preferred embodiment shown in FIG. 12C, an isometric view of an embodiment in which the administration means 18 is a cannula is shown. The cannula is in fluid connection with the drug chamber 16, and extends either directly from the housing 20, or from a tab projecting therefrom (not shown). The cannula may be a rigid one or an array of small rigid ones. In a further preferred embodiment, a flexible cannula such as the Teflon® type cannulas known in the art may be used. In the latter case, said cannula can be inserted into the patient's body by means of an insertion device. In a still further preferred embodiment, the cannula can be inserted into the body by a mechanism internal to the drug-delivery device of the present invention.

Figure 12D:
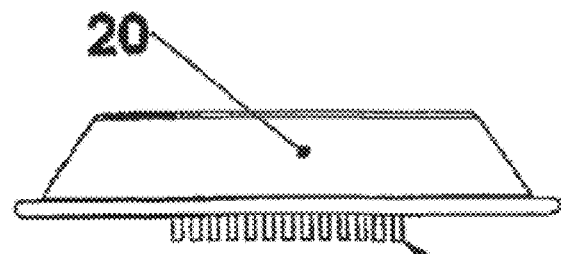

Referring now to FIG. 12D, a side view of a further preferred embodiment is provided. In this embodiment, the administration means 18 is an array of mini or micro-needles extending from the base of the housing 20 of the device. This embodiment is especially suitable for a low-profile version of the device, where only a small drug volume is required. Examples of micro-needle arrays include the Microstructured Transdermal Systems (MTS) array from 3M Drug-delivery Systems (St. Paul, Minn., USA). Advantageously, this type of array enables the disruption of the outermost layer of the skin, the stratum corneum, without causing pain; and thus the drug device of the present invention which integrates such an array can be applied to the skin in a completely painless manner.

In general, many drug-delivery device embodiments of the present invention are suitable for use as a patch-pump for delivering drug volumes between 0.5 mL and 10 mL. Embodiments at the lower end of this range can be more coin-like in shape, whereas those at the higher end can be more reminiscent of the embodiments shown in FIGS. 10A to 10C and 12A to 12D. A patch-pump of this nature can be applied to the skin in a number of manners, including but not limited to the use of adhesives, straps and such-like. It may also be desirable to automatically activate the drug-delivery device when the administration means 18 is applied to the skin, or when an auto-insertion means of a cannula is activated.

Referring now to FIGS. 13A and 13B, isometric and cross-sectional views (respectively) are shown of a pen-shaped preferred embodiment of the drug-delivery device of the present invention. In this preferred embodiment, a multiplicity of battery cells 10 as described above are arranged in series such that their combined displacement presses upon a displaceable wall 14. The displaceable wall 14 acts as a piston within the drug chamber 16; the movement of said piston 14 serving to expel the drug. In a preferred embodiment of this configuration, the pen-shape is terminated at its upper end with a Luer lock serving as the administration means 18, and the electronic control unit 12 is integrated into the pen's base. This embodiment has the advantage of efficiently exploiting the available volume, such that there is little of no "dead space" within the device's housing. Additionally, the pen form-factor is well known, easy to clip on to shirt or jacket and unobtrusive; while also obviating the need to adhere the device to the skin. According to some embodiments of the present invention, the relative location of the components within the pen shape can easily be altered, and thus it is possible, if preferred, to have the Luer lock on the bottom and the electronics at the top.

A further advantage of this embodiment is that the shape of the drug chamber 16 enables a vial with an integral piston to be used. This use of such a vial is further described in connection with FIGS. 13C, 13D and 13E, in which hydraulic coupling is utilized to couple the battery cell 10 to a vial 55. This embodiment enjoys the advantage that it may use relatively standard vials, which are typically made from glass and can hold a drug for an extended period. Such a vial 55 may be inserted into the device shown by the user, thereby reducing regulatory requirements in the development of such a device. In this preferred embodiment, the expansion of the volume-changing or shape-changing component of the cell 10 causes the contraction of a reservoir 57 containing hydraulic fluid. On said contraction, said hydraulic fluid is expelled via hydraulic conduit 56 where it presses upon a piston (not shown) at the base of said vial 55; thereby causing the drug contained within said vial 55 to be expelled. It will be clear to one skilled in the art that the coupling between the battery cell 10 and the vial 55 may be achieved via any coupling means including but not limited to mechanical bar mechanisms, mechanical trains, pulleys, and the like, resulting in either proportional motion or a more complex exponential correlation.

Figure 14A:
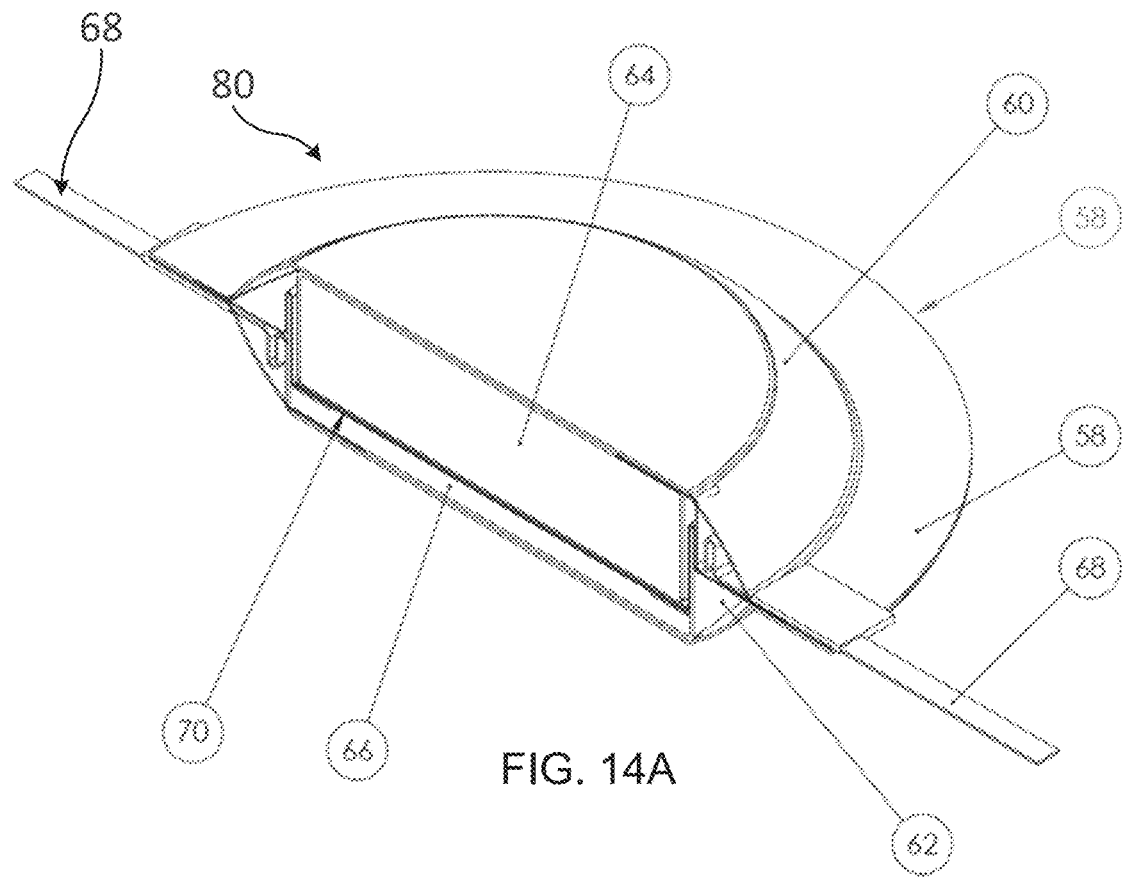
Figure 14B:
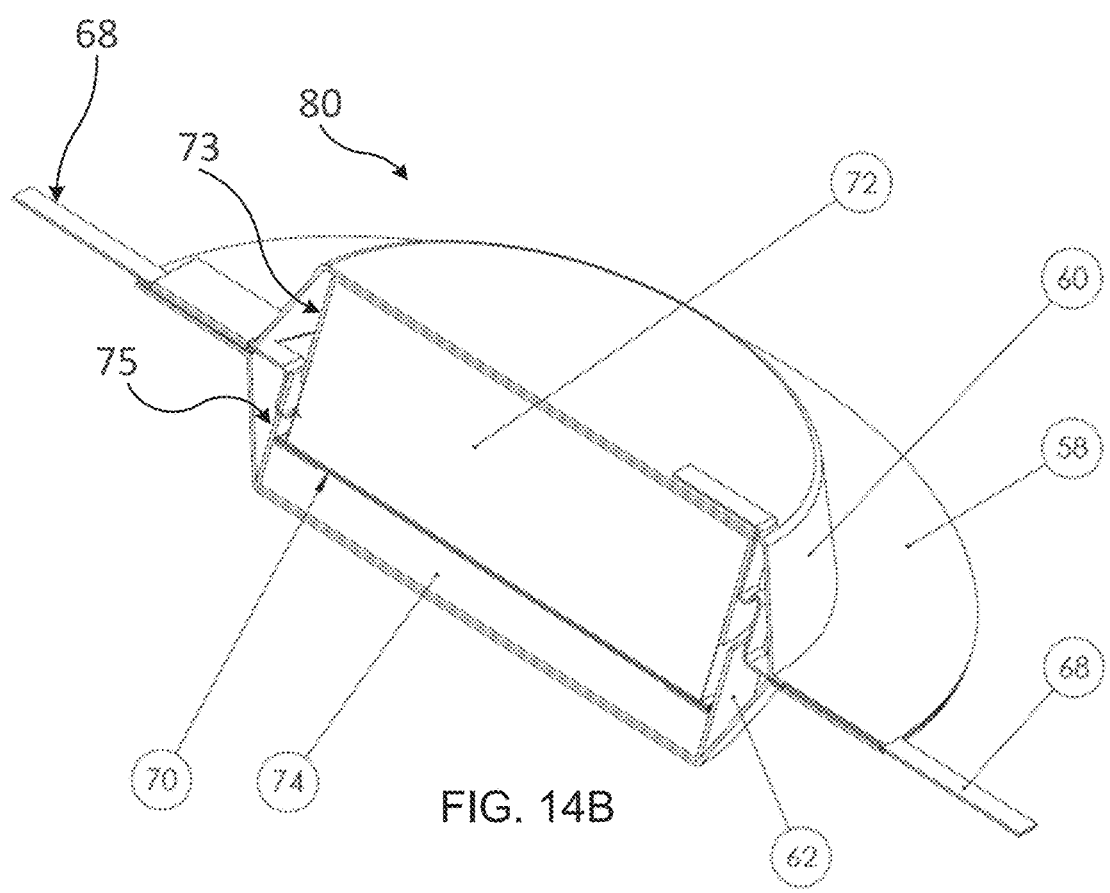

Referring now to FIGS. 14A to 14F, exemplary embodiments of a displacement-generating battery cell 80 of the present invention are shown, showing the expansion of a Zinc-Manganese dioxide battery during charge depletion. FIG. 14A shows the flexible housing 60 of this embodiment where the sides of said housing 60 are welded together at the welding seam 58 so as to produce a sealed enclosure. Said housing 60 encloses the two electrodes, in this case a manganese dioxide ($MnO_2$) cathode tablet 64 and a Zinc (Zn) anode tablet 66, separated by a separator 70, and in liquid contact with an aqueous KOH solution 62 serving as the electrolyte. Suitable materials for the separator 70 include cellulose and polyolefin, suitable materials for the housing 60 include different grades including non-woven, microporous, monolayer of polyethylene (PE), polypropylene (PP), polyamide (PA), polyvinyl chloride (PVC), or a combination of these materials like bi- or tri-layers such as PP/PE/PP. The separators 70 can also be chosen from a group that includes non-woven separators made from materials such as cellulose, cellophane, Nylon, polyvinyl acetate (PVA) and other fibrous materials. The separators 70 may be coated with surfactants. The separators 70 may also be of the laminated type.

Suitable material for the tabs 68 include titanium, nickel, brass, copper, stainless steel, steel, and optionally indium coated with or without a polyolefin partial coating. Also included within the structure are two tabs 68 or other appropriate electrical contact means, such that each tab 68 is connected to one of said electrodes (e.g. cathode 64, anode 66) via a current collector. On applying a load across said battery contacts, the battery cell 80 discharges causing a significant expansion of both anode 66 and cathode 64 relative to the initial situation shown in FIG. 14A; said expansion or displacement being conveyed externally via the housing 60, to drive the drug delivery according to embodiments of the present invention. Without wishing to be bound by theory, the chemical reactions that take place within the battery cell are as follows:

Positive reaction: $MnO_2 + H^+ e^- \rightarrow MnOOH$ negative reaction: $Zn + 2OH^- \rightarrow ZnO + H_2O + 2e^-$ total reaction: $2MnO_2 + H_2O + Zn \rightarrow 2MnOOH + ZnO$ Referring now to FIG. 14B, the final stage of this expansion is shown where the cathode 72 is now substantially comprised of MnOOH 72 and the anode 74 is now substantially comprised of ZnO. The expansion of the zinc anode tablet 74 from Zn to ZnO is typically of the order of 100% and even up to about 135%, and the expansion of the manganese cathode tablet 72 from $MnO_2$ to MnOOH is typically of the order of 50% and even up to about 75%. Given a ratio of initial heights of 1:5 between the zinc and manganese tablets, the resulting overall expansion of the battery cell 80 is thus of the order of 50% relative to the initial height. In the embodiment depicted here, the battery cell 80 also includes current collectors for each of the electrodes. For example, cathode tablet 72 is at least partially disposed within a cathode current collector 73, and anode tablet 74 is at least partially disposed within an anode current collector 75. In operation, both the cathode 72 and its corresponding anode 74 expand upon discharge of the battery. In turn, the respective current collectors 73, 75 for the cathode and anode are forced away from one another, thus also moving the translating portions of the tabs 68. Hence, both the anode 74 and the cathode 72 expand and can generate force in opposing directions during discharge.

Figure 14C:
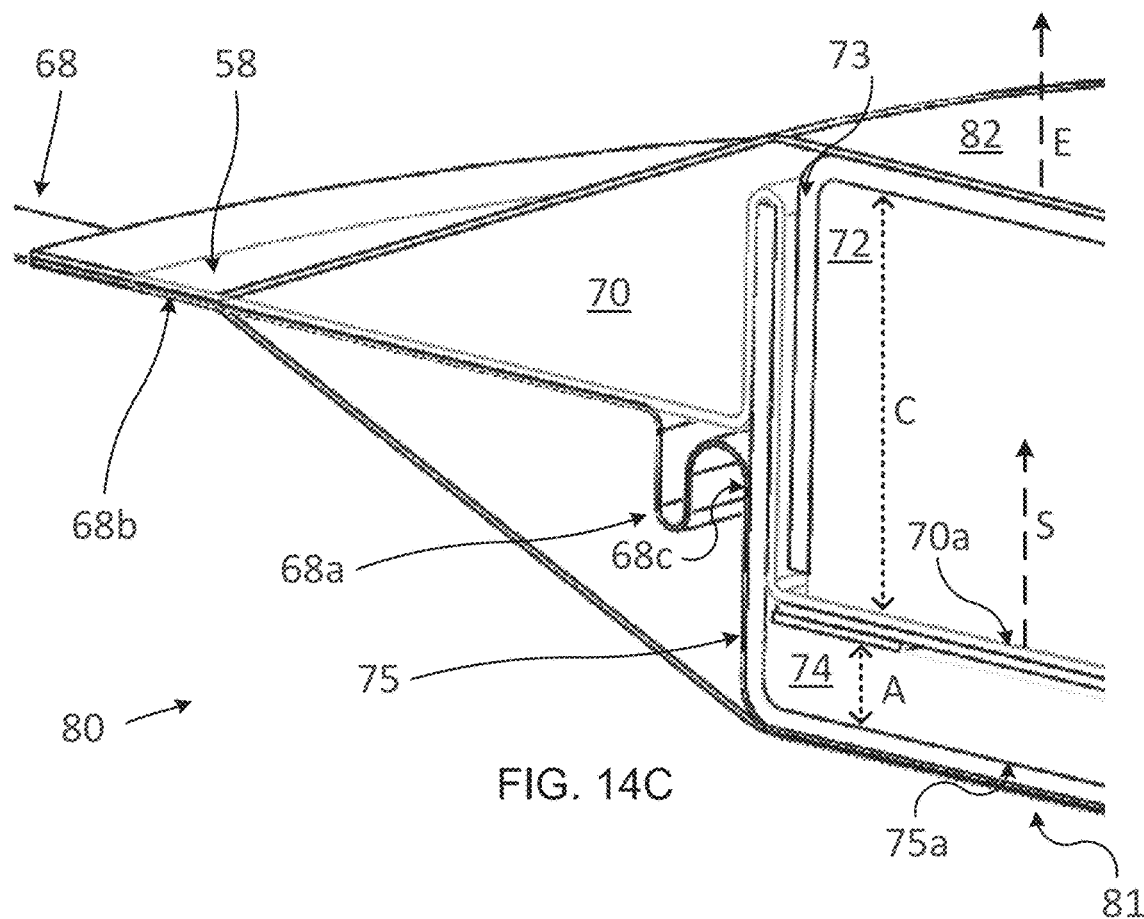

As depicted in FIG. 14C, which shows a partial close-up view of a battery cell 80 according to embodiments of the present invention, the tab 68 which is coupled with the anode collector can 75 includes a folded or accordionated portion 68a that is internal to the housing, and which accommodates the cell expansion and movement. Hence, the peripheral portion 68b of the tab can remain associated with the seam 58, while the central portion 68c remains associated with the anode current collector 75. When the anode 74 expands (as indicated by arrow A) and/or when the cathode 72 expands (as indicated by arrow C), the folded portion 68a facilitates relative freedom of movement between the anode collector can 75 and the peripheral portion 68b of the tab. For example, expansion of anode 74 can operate to drive a central portion 70a of the separator 70 away from a central portion 75a of the anode current collector 75, as indicated by arrow S. As discussed elsewhere herein, in some instances the bottom (as shown here) surface or portion 81 of the housing or cell can be fixed to a printed circuit board or some other rigid element. In such cases, expansion of anode 74 and/or cathode 72 can operate to drive the upper (as shown here) surface or portion 82 of the housing or cell in the direction indicated by arrow E. Accordingly, by virtue of providing a portion of the tab internal to the housing that is folded like an accordion, such a configuration can accommodate the cell expansion and movement. In some instances, expansion of either or both of the electrodes 72, 74, can operate to force the top plate or portion 82 and bottom plate or portion 81 of the housing or cell away from each other in opposing directions, for example relative to the central separator section 70a. As shown in FIG. 14C, the current collectors can be in a nested orientation. For example, the cathode 72 and the cathode current collector 73 can be nested or at least partially disposed within the anode current collector 75.

Figure 14D:
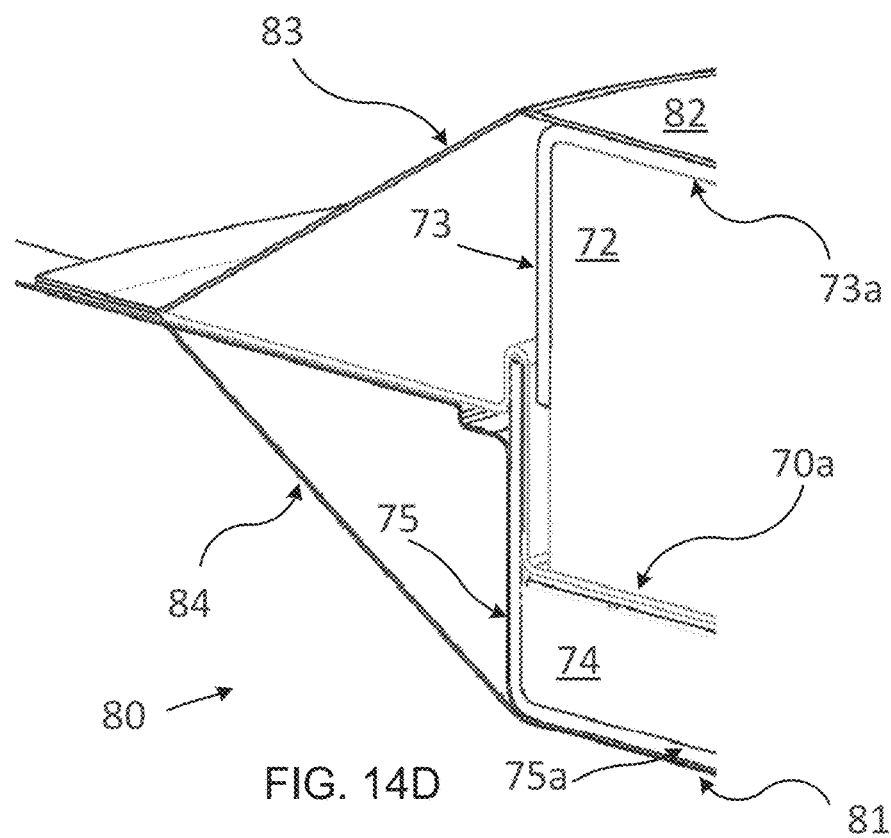

FIG. 14D depicts the configuration of a cell 80 following expansion, according to embodiments of the present invention. As shown here, the dimensions of the electrodes 72, 74 are increased relative to their dimensions show in FIG. 14C. For example, expansion of anode 74 can operate to press the separator central section 70a and the anode current collector central section 75a away from one another. Where the current collector central section 75a is fixed (e.g. bottom portion 81 of battery cell is mounted on a circuit board or some other object), expansion of the anode 74 can operate to press the separator central section 70a away from that board or object. Or vice versa, where the upper portion 82 of the battery cell is fixed to an object, expansion of the anode 74 can operate to force the current collector central section 75a away from that object (and away from the separator central section 70a. Similarly, expansion of cathode 72 can operate to press the separator central section 70a and the cathode current collector central section 73a away from one another. Where the bottom portion 81 of the battery cell is fixed to an object, expansion of the cathode 72 can operate to force the cathode current collector central section 73a away from the object (and away from the separator central section 70a). Or vice versa, where the upper portion 82 of the battery cell is fixed to an object, expansion of the cathode 72 can operate to force the separator central section 70a away from the object (and away from the cathode current collector central section 73a. Relatedly, a first housing portion (upper, as shown here) 83 and a second housing portion 84 (lower, as shown here) are now further separated from one another, in comparison to the configuration depicted in FIG. 14C. Further, the geometry of the accordion tab 68 has changed. According to some embodiments, expansion of anode 74 operates to press the central section 70a of the separator sheet 70 upward, and there is a sliding interface between the anode current collector 75 and the separator sheet 70. In some instances, the separator sheet 70 can be pushed up following the expansion front. As depicted in FIG. 14D, expansion of the cathode 72, the anode 74, or both, can operate to provide an increased separation between the current collectors 73, 75.

As discussed elsewhere herein, a battery cell 80 can be used in a pump mechanism for dispensing a medicament. For example, the battery cell can be mounted on or fixed to a printed circuit board (PCB), which may have a substantial thickness or rigidity such that the PCB does not bend when the battery cell expands. In such cases, during or as a result of expansion of the anode 74, the cathode 72, or both, the battery cell can operate as an actuator in a pump. Where a battery cell is mounted on or fixed to such an object, the cell as a whole expands in one direction, namely away from the object (e.g. printed circuit board).

Figure 14E:
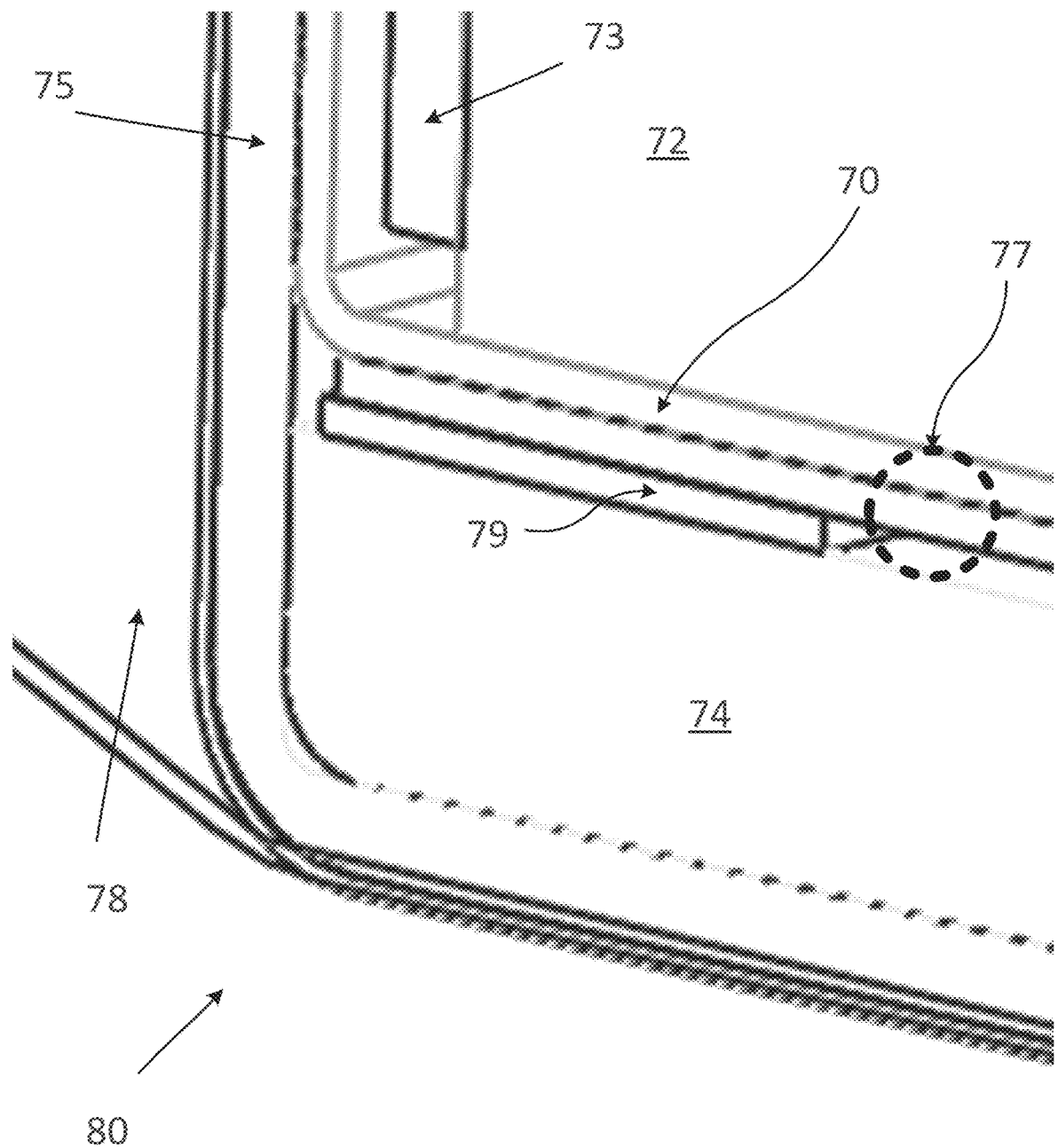

FIG. 14E provides a close up view of the interface between the cathode 72 and the anode 74, with the separator 70 and a ring or gasket 79 disposed therebetween. The separator 70 physically separates the anode 74 and cathode 72 and also operates the anode 74 and cathode 72 by functioning as an absorbent for a liquid electrolyte. As shown here, the separator 70 also extends between the anode current collector 75 and the cathode current collector 73. In operation, the separator serves as an ion conducting pathway from the electrolyte reservoir 78 to a space or zone 77 between the anode 74 and the cathode 72. According to some embodiments, the ring or gasket 79 is a poly-ethylene ring that functions to minimize or inhibit the portion of the anode 74 directly underneath from reacting and thereby expanding. In this way, the presence of the gasket 79 leaves an unexpanded or less expanded portion of the anode 74. Accordingly, that unexpanded or less expanded portion of the anode 74 does not compress or squeeze the separator 70 against the cathode 72. In this way, the uncompressed or less compressed section of the separator 70 can maintain a sufficient flow of electrolyte from outside of the collector 75 (e.g. from reservoir 78) to the interface 77 between the anode 74 and the cathode 72. Where there is significant compression of the separator 70 between the anode 74 and the cathode 72, electrolyte may not be able to freely flow to the interface via the separator 70. Hence, in the absence of the ring 79, the peripheral area or edge of the anode 74 may expand, thus squeezing the corresponding area of the separator 70, and thereby restricting or preventing the ingress of electrolyte via the separator 70 to the space 77. According to some embodiments, only parallel surface areas between the two electrodes 72, 74 react. In some instances, the relative participation of the anode and cathode in terms of expansion areas is coextensive. In the embodiment depicted here, the diameter of the anode 74 is greater than the diameter of the cathode 72. According to some embodiments, the area of the cathode 72 that faces the ring 79 does not participate in the expansion. Thus, the ring 79 can block expansion of the anode and the cathode areas that face it. Relatedly, the ring 79 also can be viewed as affecting the shape of the expansion of the anode 74 and the cathode 72, meaning that the areas of the electrodes corresponding to or aligned with the center of the ring 79 expand while those areas covered by the ring generally do not expand, thus leading to the formation of a step between an expanded electrode portion and an unexpanded (or relatively less expanded) electrode portion. According to some embodiments, it is possible to prevent or inhibit compression of the separator edge by placing the ring 79 instead on the other side of the separator 70, that is between the separator 70 and the cathode 72. According to some embodiments, the anode current collector 75 can be constructed of brass that is plated with indium. In some embodiments, the cathode current collector 73 can be constructed of pure nickel, nickel plated steel, or stainless steel. The accordion tab can be attached to the anode current collector can 75 using resistance welding.

FIG. 14F depicts a battery cell 80 within a pump mechanism 90, in positional relationship to a drug container or reservoir 92. The pump mechanism 90 shown here also includes a magnet 94 that can generate a magnetic field which is sensed by a Hall effect sensor 96, as discussed elsewhere herein. Together, the magnet 94 and the Hall effect sensor 96 can be included in a position control unit. According to some embodiments, the battery cell 80 can be mounted on or fixed relative to a printed circuit board 98 or other similar support or surface. As the battery cell 80 expands, the magnet 94 moves further from the Hall Sensor 96. In turn, the Hall Sensor 96 can detect the magnitude of the field which can be translated into distance to determine the extent of the expansion. As shown here, magnet 94 interfaces with the piston 99, which can operate to translate the expansion of the battery cell 80 to the compression of the drug reservoir or chamber 92.

Figure 15:
FIG. 15 shows aspects of an exemplary drug-delivery device according to embodiments of the present invention.
Figure 15:

FIG. 15 shows aspects of an exemplary drug-delivery device according to embodiments of the present invention. Specifically, FIG. 15 depicts a drug delivery device 1500 comprising a battery recharging means 1510.

FIG. 16 shows aspects of an exemplary drug-delivery device according to embodiments of the present invention. Specifically, FIG. 16 depicts a drug delivery device that is a patch-type pump 1600. The patch-type pump 1600 is attached to the body of a user 1620 by an attachment means 1610. The attachment means 1610 may include an adhesion means, a strap, a clasp, and combinations thereof.

Figure 17:
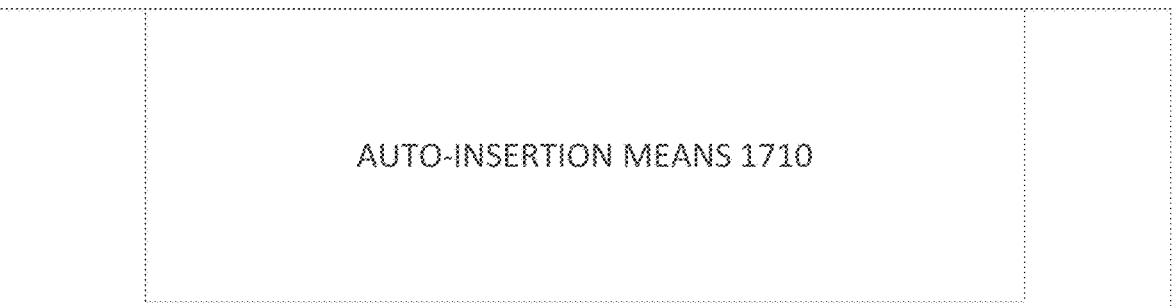
FIG. 17 shows aspects of an exemplary drug-delivery device according to embodiments of the present invention.
Figure 17:
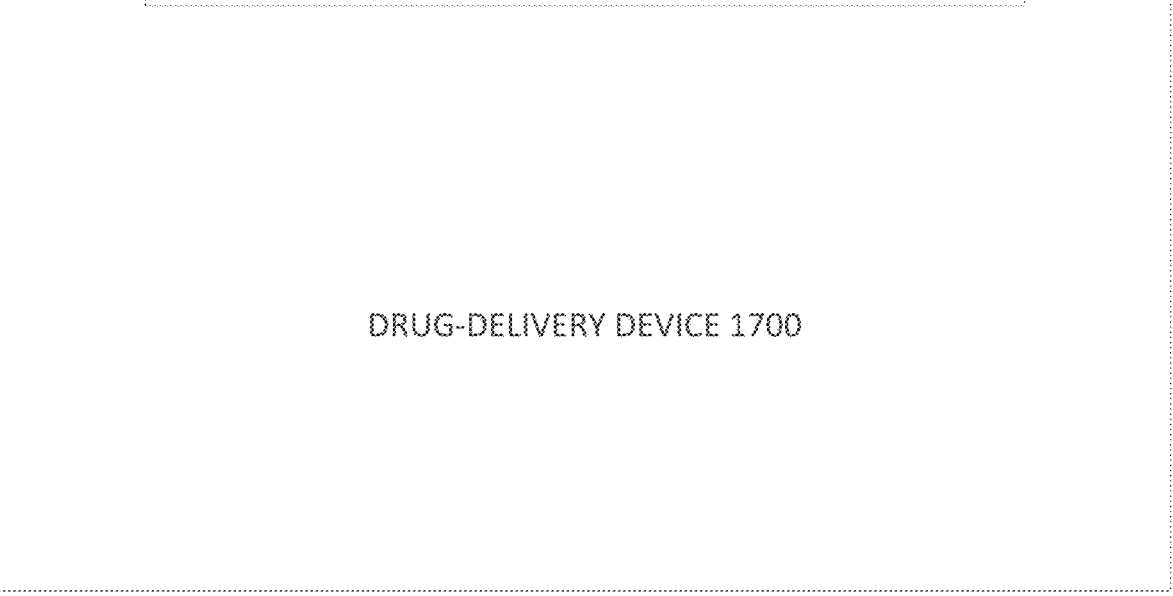

FIG. 17 shows aspects of an exemplary drug-delivery device according to embodiments of the present invention. Specifically, FIG. 17 depicts a drug delivery device 1700 comprising an auto insertion means 1710.

FIG. 18 shows aspects of an exemplary drug-delivery device according to embodiments of the present invention. Specifically, FIG. 18 depicts a drug delivery device 1800 comprising a means for mixing 1810.

Figure 19:
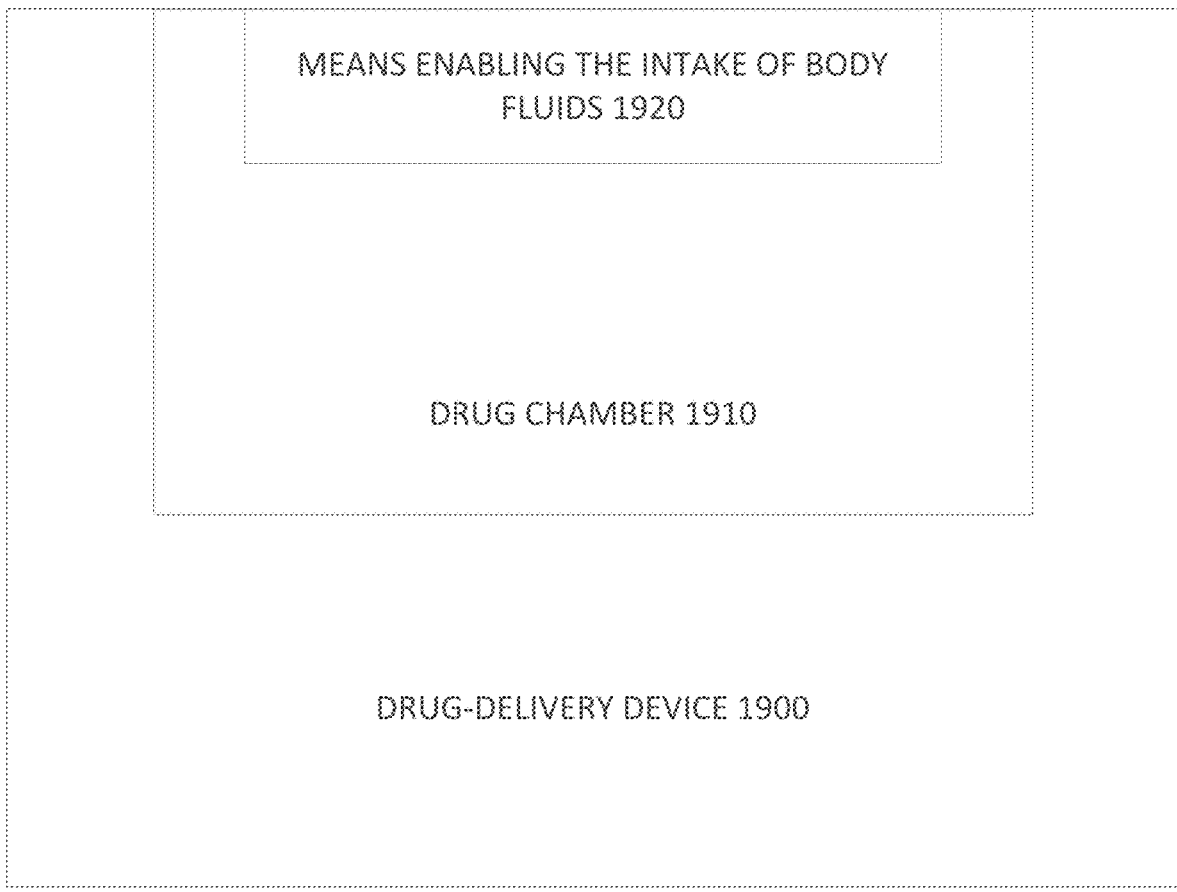
FIG. 19 shows aspects of an exemplary drug-delivery device according to embodiments of the present invention.

FIG. 19 shows aspects of an exemplary drug-delivery device according to embodiments of the present invention. Specifically, FIG. 19 depicts a drug delivery device 1900 having a drug chamber 1910, the drug chamber 1910 comprising means enabling the intake of body fluids 1920.

FIG. 20 shows aspects of an exemplary drug-delivery device according to embodiments of the present invention. Specifically, FIG. 20 depicts a drug delivery device 2000 having a means for sampling body fluids 2010.

FIG. 21 shows aspects of an exemplary drug-delivery device according to embodiments of the present invention. Specifically, FIG. 21 depicts a drug delivery device 2100 having a communication means 2110.

FIG. 22 shows aspects of an exemplary drug-delivery device according to embodiments of the present invention. Specifically, FIG. 22 depicts a drug delivery device 2200 having a safety feature 2210.

Figure 23:
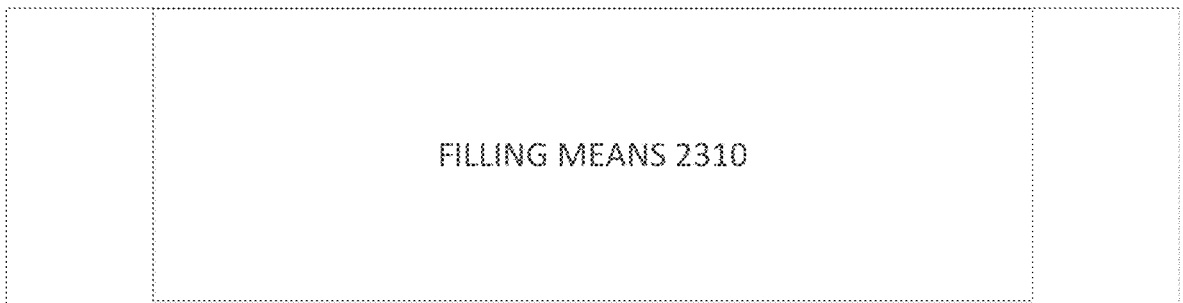
FIG. 23 shows aspects of an exemplary drug-delivery device according to embodiments of the present invention.
Figure 23:

FIG. 23 shows aspects of an exemplary drug-delivery device according to embodiments of the present invention. Specifically, FIG. 23 depicts a drug delivery device 2300 having a filling means 2310.

It will be noted that while exemplary embodiments employ an expanding element within the battery cell as disclosed herein, it will be clear to one skilled in the art that the drug-delivery device could equally well be driven by a contracting element within said cell, by changing the mechanical operation. Examples of this approach are shown hereinabove. Additionally, springs may advantageously be incorporated into the device in a number of configurations. For example, embodiments described above can achieve greater stability by having the driving force partially counterbalanced by an opposing spring. This will ensure smoother movement and provide greater artifact resistance. In a further preferred embodiment, the spring can provide the driving force while the cell serves as a brake. The advantages of this approach and further details of its implementation are described in International Publication No. WO 2004/067066, which is incorporated herein by reference. According to some embodiments of the present invention, the connection between the battery cell and the drug chamber can be any kind of mechanical, hydraulic, magnetic or other coupling means known in the art; and said coupling action may result in either a proportional or an exponential correlation between a multiplicity of such drug chambers and a multiplicity of such cells. Note that in certain systems according to this embodiment the driving force will be the combination of the force exerted by the spring and the contraction/expansion of the cell.

Whereas the embodiments above describe relatively simple configurations of the drug-delivery device of the present invention, the general principles involved in such embodiments of the invention enable the implementation of a large number of further embodiments; said further embodiments addressing further issues in such devices, such as refilling, drug dilution, delivery of a multiplicity of drugs (with or without mixing) and the fabrication of sophisticated implantable versions. For example, a combination of two cells driving in opposite direction may be employed in order to enable two-way motion of a drug chamber piston in order to allow refilling of the drug chamber. Similarly, if it is desired to provide an implantable drug-delivery device which is able to work over an extended period, a second drug chamber containing a highly-concentrated form of the drug to be delivered can be incorporated. In a preferred embodiment, a small amount of said drug concentrate from the second or reservoir chamber is introduced to the drug chamber while body fluids are also introduced into said drug chamber to dilute it. In this way, further described in patent application IL 169,807, the content of which is incorporated herein by reference, the drug chamber is re-filled using a concentrate and then may resume its slow-infusion mode of operation. According to some embodiments of the present invention, the concentrated drug can be in either liquid or solid form, and the mechanism as described above can provide drug-delivery over an extended period without requiring external refilling. Likewise, the ability to use the drug-delivery device of the present invention to perform intake of body fluids enables said device to further incorporate various body fluid sampling and/or analysis elements.

In another preferred embodiment, the drug delivery device is driven by a displacement-generating battery, such battery increasing its volume due to an electrochemical reaction that discharges the battery; where such volume expansion actuates a coupling device to expel a drug from the drug chamber via an administration means to the patient.

In yet another preferred embodiment, the drug delivery device is driven by a displacement-generating battery containing an expanding electrode which expands due to cell discharge and whose volume expansion can be exploited to actuate a coupling device to expel a drug from the drug chamber via an administration means to the patient.

Regarding the electrical or electronic control circuit of the drug-delivery device, according to some embodiments of the present invention a wide range of electronic control systems (not shown) may be incorporated within (or interfaced to) said device. Said range includes: (a) microprocessor-controlled variable-resistance or load elements for controlled discharge of the cell; (b) removable control units that enable a semi-disposable device to be constructed whereby all or part of the control circuitry may be moved from disposable section to disposable section; (c) systems comprising a remote-control element; (d) systems that interface to a flow-control feedback element monitoring the actual drug-delivery rate, either directly or indirectly; (e) an interface control unit that receives signals related to medical parameters such as blood-glucose levels, other blood-analyte levels and body temperature; and (f) any combination of the above. Advantageously, said electronics circuit and/or electronic control systems may be at least partially powered by the very depletion of power that drives the drug-delivery device, thereby in many cases obviating the need to provide a battery to power the electronics of such a device. Additionally, in the case of an implanted device, the design may further employ embedded electronics sealed by resin casting or other sealing means known in the art, and various communication means including but not limited to magnetic coupling transmission, RF or IR transmission.

Preferred chemical systems for the battery cell of the drug-delivery device according to embodiments of the present invention are those which are non-gassing or in which there is minimal parasitic gas production. Nevertheless, in the case that the selected chemical reaction does generate gas and the mechanical embodiment is sensitive to gas (note that the embodiments with high counter force are less sensitive to gas) said gas may either be vented via a gas-permeable membrane or recombined via a catalytic plug such as those made by Hoppecke Battery Company, Germany. According to some embodiments, cell walls other than the displaceable one can remain fixed and rigid in order to maintain the accuracy of the slow-infusion device, and it may be important that such membrane be provided with an appropriate support structure so as not to detract from the rigid structure of the cell. These gas eliminating means are arranged in a fashion that efficiently operates in every operational orientation of the device. Suitable gas-permeable membranes include Fluoropore™ membrane from Millipore Inc. (Billerica, Mass., USA) and Emflon™ from Pall Inc. (East Hills, N.Y., USA).

All patents, patent publications, patent applications, journal articles, books, technical references, and the like discussed in the instant disclosure are incorporated herein by reference in their entirety for all purposes.

While the invention has been shown herein in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent structures and devices.

What is claimed is:

1. A displacement-generating battery cell for driving a drug-delivery device and comprising at least one volume-changing element, said cell comprising a housing formed according to a concertina-shaped design with folds in the walls thereof and containing an internal chemical reaction system, wherein the housing is a pole of the displacement-generating battery cell, said chemical reaction system comprising an electrode, said electrode being porous and being said volume-changing element, and the arrangement of said chemical reaction system being such that:

an expansion of the volume-changing element in a direction lengthens the cell and thus reduces the extent of said folds.

2. The displacement-generating battery cell of claim 1, wherein:

the chemical reaction system is configured such that discharging of the cell results in the expansion of the volume-changing element by ions from an electrolyte penetrating the electrode.

3. The displacement-generating battery cell of claim 1, further comprising a mesh surrounding the electrode.

4. The displacement-generating battery cell of claim 3, wherein:
the direction is a first direction, and
the mesh prevents expansion of the electrode in a second direction.

5. The displacement-generating battery cell of claim 3, wherein the mesh is stainless steel.

6. The displacement-generating battery cell of claim 1, wherein:
the chemical reaction system being configured such that discharging of the cell results in the expansion of the volume-changing element in the direction.

7. The displacement-generating battery cell of claim 1, wherein the electrode is on a printed circuit board.

8. The displacement-generating battery cell of claim 1, wherein at least one component of the displacement-generating battery cell undergoes a volume change of at least 30%.

9. The displacement-generating battery cell of claim 1, the arrangement of said chemical reaction system further being such that a contraction of the volume-changing element in the direction shortens the cell and thus increases the extent of said folds, and
the chemical reaction system being configured such that charging the cell results in the contraction of the volume-changing element in the direction.

10. The displacement-generating battery cell of claim 1, wherein said chemical reaction system is chosen from the group consisting of Li—Sn, (Li)LiC$_6$—Sn, Fe—LaNi$_5$, lithium-lead, lithium-antimony, lithium-silicon and lithium bismuth.

11. The displacement-generating battery cell of claim 1, wherein the electrode comprises tin.

12. The displacement-generating battery cell of claim 1, wherein:
the electrode is a first electrode,
the displacement-generating battery cell further comprising a second electrode, the second electrode comprising lithium.

13. The displacement-generating battery cell of claim 1, further comprising an organic solvent or a polymer electrolyte together with a lithium ion-providing salt.

14. The displacement-generating battery cell of claim 1, further comprising an electrolyte, and the electrolyte comprises a solvent of a mixture of ethylene carbonate and ethyl methyl carbonate with dissolved lithium hexafluorophosphate.

15. The displacement-generating battery cell of claim 1, wherein the chemical reaction is non-gassing.

16. The displacement-generating battery cell of claim 1, wherein:
the electrode is a tin cathode, and
the displacement-generating battery cell further comprises a lithium anode.

17. The displacement-generating battery cell of claim 1, further comprising a cap, wherein:
the pole is a first pole of the displacement-generating battery cell,
the cap is a second pole of the displacement-generating battery cell, and
the expansion of the volume-changing element moves the cap in the direction.

* * * * *